US011850277B2

(12) United States Patent
Meenan et al.

(10) Patent No.: US 11,850,277 B2
(45) Date of Patent: *Dec. 26, 2023

(54) TREATMENT OF LOWER URINARY TRACT EPITHELIUM WITH GLUCAGON LIKE PEPTIDE 2

(71) Applicant: URIGEN N.A., North Brunswick, NJ (US)

(72) Inventors: Christopher P. Meenan, Kinnelon, NJ (US); C. Lowell Parsons, Henderson, NV (US); Daniel Vickery, Highland Park, NJ (US)

(73) Assignee: URIGEN N.A.

( * ) Notice: Subject to any disclaimer, the term of this patent is extended or adjusted under 35 U.S.C. 154(b) by 209 days.

This patent is subject to a terminal disclaimer.

(21) Appl. No.: 17/153,394

(22) Filed: Jan. 20, 2021

(65) Prior Publication Data

US 2021/0145938 A1 May 20, 2021

Related U.S. Application Data

(63) Continuation of application No. 16/488,628, filed as application No. PCT/US2018/019949 on Feb. 27, 2018, now Pat. No. 10,925,930.

(60) Provisional application No. 62/463,923, filed on Feb. 27, 2017.

(51) Int. Cl.
*A61K 38/26* (2006.01)
*A61P 13/10* (2006.01)
*A61K 45/06* (2006.01)

(52) U.S. Cl.
CPC ............. *A61K 38/26* (2013.01); *A61P 13/10* (2018.01); *A61K 45/06* (2013.01)

(58) Field of Classification Search
CPC ......... A61K 38/26; A61K 45/06; A61P 13/10; A61P 13/02
See application file for complete search history.

(56) References Cited

U.S. PATENT DOCUMENTS

| 6,449,512 B1 * | 9/2002 | Boveja ............... A61N 1/37217 607/30 |
| 10,925,930 B2 * | 2/2021 | Meenan ................ A61P 13/02 |
| 2007/0135345 A1 | 6/2007 | Henriksen et al. |
| 2010/0303794 A1 | 12/2010 | Francis et al. |

FOREIGN PATENT DOCUMENTS

| WO | 2012/051431 A2 | 4/2012 |
| WO | 20150127416 A1 | 8/2015 |

OTHER PUBLICATIONS

Drucker et al. "Induction of intestinal epithelial proliferation by glucagon-like peptide 2," Proceedings of the NAtional Academy of Sciences, vol. 93 No. 15, 1996. pp. 7911-7916.
Jeppesen et al. "Randomised placebo-controlled trial of teduglutide in reducing parenteral nutrition and/or intravenous fluid requirements in parenteral nutrition and/or intravenous fluid requirements in patients with short bowel syndrome," Gut, vol. 60, pp. 902-914 (2011).
Villanueva et al., "Short Communication: Effect of Glucagon-Like Peptide 2 on Hepatic, Renal, and Intestinal Disposition of 1-Chloro-2,4-dinitrobenzene," Drug Metabolism and Disposition, vol. 40, No. 7, pp. 1252-1258 (2012).
International Search Report and Written Opinion to corresponding International Application No. PCT/US2018/019949, dated May 23, 2018, 8 pages.

* cited by examiner

*Primary Examiner* — Marcela M Cordero Garcia
(74) *Attorney, Agent, or Firm* — Greenberg Traurig, LLP; Barry Schindler; Natalie Salem

(57) ABSTRACT

The present invention provides a method for treating and/or ameliorating a disorder of the lower urinary tract, comprising administering a composition comprising a glucagon like peptide 2 (GLP-2) receptor agonist to a patient in need thereof in an amount sufficient to treat and/or ameliorate the disorder of the lower urinary tract.

17 Claims, 2 Drawing Sheets

Specification includes a Sequence Listing.

SEQUENCE LISTING

<160> NUMBER OF SEQ ID NOS: 63

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Arg, Lys, His, or absent
<220> FEATURE:
<221> NAME/KEY: MOD_RES
<222> LOCATION: (2)..(2)
<223> OTHER INFORMATION: Arg, Lys, His, or absent
<220> FEATURE:
<221> NAME/KEY: MOD_RES
<222> LOCATION: (3)..(3)
<223> OTHER INFORMATION: His or Tyr
<220> FEATURE:
<221> NAME/KEY: MOD_RES
<222> LOCATION: (4)..(4)
<223> OTHER INFORMATION: Ala or an Ala-replacement amino acid conferring
      on said analog resistance to DPP-IV enzyme
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (11)..(11)
<223> OTHER INFORMATION: Glu or Tyr
<220> FEATURE:
<221> NAME/KEY: MOD_RES
<222> LOCATION: (12)..(12)
<223> OTHER INFORMATION: Ser if position 11 is Tyr, otherwise Met or an
      oxidatively stable Met replacement amino acid
<220> FEATURE:
<221> NAME/KEY: MOD_RES
<222> LOCATION: (13)..(13)
<223> OTHER INFORMATION: Lys if position 11 is Tyr, or Asn
<220> FEATURE:
<221> NAME/KEY: MOD_RES
<222> LOCATION: (14)..(14)

<223> OTHER INFORMATION: Tyr if position 11 is Tyr, or Thr
<220> FEATURE:
<221> NAME/KEY: MOD_RES
<222> LOCATION: (15)..(15)
<223> OTHER INFORMATION: Ile, or Xaa is not present if position 11 is
      Tyr
<220> FEATURE:
<221> NAME/KEY: MOD_RES
<222> LOCATION: (21)..(21)
<223> OTHER INFORMATION: Ala or Thr
<220> FEATURE:
<221> NAME/KEY: MOD_RES
<222> LOCATION: (22)..(22)
<223> OTHER INFORMATION: Arg, Lys, His, or Ala
<220> FEATURE:
<221> NAME/KEY: MOD_RES
<222> LOCATION: (25)..(25)
<223> OTHER INFORMATION: Ile or Val
<220> FEATURE:
<221> NAME/KEY: MOD_RES
<222> LOCATION: (26)..(26)
<223> OTHER INFORMATION: Asn or Ala if position 25 is Ile, Gln if
      position 25 is Val
<220> FEATURE:
<221> NAME/KEY: MOD_RES
<222> LOCATION: (33)..(33)
<223> OTHER INFORMATION: Ile or a covalent bond
<220> FEATURE:
<221> NAME/KEY: MOD_RES
<222> LOCATION: (34)..(34)
<223> OTHER INFORMATION: Thr if position 34 is Ile, or a covalent bond
<220> FEATURE:
<221> NAME/KEY: MOD_RES
<222> LOCATION: (35)..(35)
<223> OTHER INFORMATION: Asp if position 35 is Thr, or a covalent bond
<220> FEATURE:
<221> NAME/KEY: MOD_RES
<222> LOCATION: (36)..(36)
<223> OTHER INFORMATION: Arg, Lys, His, or absent
<220> FEATURE:
<221> NAME/KEY: MOD_RES
<222> LOCATION: (37)..(37)
<223> OTHER INFORMATION: Arg, Lys, His, or absent

<400> SEQUENCE: 3

Xaa Xaa Xaa Xaa Xaa Xaa Ser Phe Ser Asp Xaa Xaa Xaa Xaa Xaa Leu
1               5                   10                  15

Asp Asn Leu Ala Xaa Xaa Asp Phe Xaa Xaa Trp Leu Ile Gln Thr Lys
            20                  25                  30

Xaa Xaa Xaa Xaa Xaa
        35

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Met or an oxidatively stable Met replacement

<400> SEQUENCE: 4

Glu Xaa Asn Thr Ile
1               5

<210> SEQ ID NO 5
<211> LENGTH: 4
<212> TYPE: PRT
<213> ORGANISM: Unknown
<220> FEATURE:

```
<223> OTHER INFORMATION: Description of Unknown:
      GLP-2 analogue

<400> SEQUENCE: 5

Tyr Ser Lys Tyr
1

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Arg or absent
<220> FEATURE:
<221> NAME/KEY: MOD_RES
<222> LOCATION: (2)..(2)
<223> OTHER INFORMATION: Arg or absent
<220> FEATURE:
<221> NAME/KEY: MOD_RES
<222> LOCATION: (15)..(15)
<223> OTHER INFORMATION: Neutral/polar/large/nonaromatic residue such as
      Ile or Val
<220> FEATURE:
<221> NAME/KEY: MOD_RES
<222> LOCATION: (18)..(18)
<223> OTHER INFORMATION: Neutral/polar residue such as Asn or Ser
<220> FEATURE:
<221> NAME/KEY: MOD_RES
<222> LOCATION: (21)..(21)
<223> OTHER INFORMATION: Neutral residue such as Ala or Thr
<220> FEATURE:
<221> NAME/KEY: MOD_RES
<222> LOCATION: (29)..(29)
<223> OTHER INFORMATION: Neutral/polar/large/nonaromatic residue such as
      Ile or Leu
<220> FEATURE:
<221> NAME/KEY: MOD_RES
<222> LOCATION: (30)..(30)
<223> OTHER INFORMATION: Neutral or basic residue such as Gln or His
<220> FEATURE:
<221> NAME/KEY: MOD_RES
<222> LOCATION: (36)..(36)
<223> OTHER INFORMATION: Arg, Lys, or absent
<220> FEATURE:
<221> NAME/KEY: MOD_RES
<222> LOCATION: (37)..(37)
<223> OTHER INFORMATION: Lys or absent

<400> SEQUENCE: 6

Xaa Xaa His Ala Asp Gly Ser Phe Ser Asp Glu Met Asn Thr Xaa Leu
1               5                   10                  15

Asp Xaa Leu Ala Xaa Arg Asp Phe Ile Asn Trp Leu Xaa Xaa Thr Lys
            20                  25                  30

Ile Thr Asp Xaa Xaa
            35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Arg or absent
<220> FEATURE:
```

```
<221> NAME/KEY: MOD_RES
<222> LOCATION: (2)..(2)
<223> OTHER INFORMATION: Arg or absent
<220> FEATURE:
<221> NAME/KEY: MOD_RES
<222> LOCATION: (21)..(21)
<223> OTHER INFORMATION: Neutral residue such as Ala or Thr
<220> FEATURE:
<221> NAME/KEY: MOD_RES
<222> LOCATION: (36)..(36)
<223> OTHER INFORMATION: Arg, Lys, or absent
<220> FEATURE:
<221> NAME/KEY: MOD_RES
<222> LOCATION: (37)..(37)
<223> OTHER INFORMATION: Lys or absent

<400> SEQUENCE: 7

Xaa Xaa His Ala Asp Gly Ser Phe Ser Asp Glu Met Asn Thr Ile Leu
1               5                   10                  15

Asp Asn Leu Ala Xaa Arg Asp Phe Ile Asn Trp Leu Ile Gln Thr Lys
            20                  25                  30

Ile Thr Asp Xaa Xaa
        35

<210> SEQ ID NO 8
<211> LENGTH: 33
<212> TYPE: PRT
<213> ORGANISM: Unknown
<220> FEATURE:
<223> OTHER INFORMATION: Description of Unknown:
      GLP-2 analogue

<400> SEQUENCE: 8

His Ala Asp Gly Ser Phe Ser Asp Glu Met Asn Thr Ile Leu Asp Asn
1               5                   10                  15

Leu Ala Thr Arg Asp Phe Ile Asn Trp Leu Ile Gln Thr Lys Ile Thr
            20                  25                  30

Asp

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, Arg, Lys, or absent
<220> FEATURE:
<221> NAME/KEY: MOD_RES
<222> LOCATION: (2)..(2)
<223> OTHER INFORMATION: His, Arg, Lys, or absent
<220> FEATURE:
<221> NAME/KEY: MOD_RES
<222> LOCATION: (15)..(15)
<223> OTHER INFORMATION: Met, Leu, Ile, Val, or Cys
<220> FEATURE:
<221> NAME/KEY: MOD_RES
<222> LOCATION: (18)..(18)
<223> OTHER INFORMATION: Ala, Ser, Thr, Pro, Gly, Asn, Asp, Glu, or Gln
<220> FEATURE:
<221> NAME/KEY: MOD_RES
<222> LOCATION: (21)..(21)
<223> OTHER INFORMATION: Ala, Ser, Thr, Pro, or Gly
<220> FEATURE:
<221> NAME/KEY: MOD_RES
<222> LOCATION: (22)..(22)
<223> OTHER INFORMATION: His, Arg, or Lys
<220> FEATURE:
```

```
<221> NAME/KEY: MOD_RES
<222> LOCATION: (29)..(29)
<223> OTHER INFORMATION: Met, Leu, Ile, Val, or Cys
<220> FEATURE:
<221> NAME/KEY: MOD_RES
<222> LOCATION: (30)..(30)
<223> OTHER INFORMATION: Asn, Asp, Glu, Gln, His, Arg, or Lys
<220> FEATURE:
<221> NAME/KEY: MOD_RES
<222> LOCATION: (36)..(36)
<223> OTHER INFORMATION: His, Arg, Lys, or absent
<220> FEATURE:
<221> NAME/KEY: MOD_RES
<222> LOCATION: (37)..(37)
<223> OTHER INFORMATION: His, Arg, Lys, or absent

<400> SEQUENCE: 9

Xaa Xaa His Ala Asp Gly Ser Phe Ser Asp Glu Met Asn Thr Xaa Leu
1               5                   10                  15

Asp Xaa Leu Ala Xaa Xaa Asp Phe Ile Asn Trp Leu Xaa Xaa Thr Lys
            20                  25                  30

Ile Thr Asp Xaa Xaa
            35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, Arg, Lys, or absent
<220> FEATURE:
<221> NAME/KEY: MOD_RES
<222> LOCATION: (2)..(2)
<223> OTHER INFORMATION: His, Arg, Lys, or absent
<220> FEATURE:
<221> NAME/KEY: MOD_RES
<222> LOCATION: (21)..(21)
<223> OTHER INFORMATION: Ala, Ser, Thr, Pro, or Gly
<220> FEATURE:
<221> NAME/KEY: MOD_RES
<222> LOCATION: (36)..(36)
<223> OTHER INFORMATION: His, Arg, Lys, or absent
<220> FEATURE:
<221> NAME/KEY: MOD_RES
<222> LOCATION: (37)..(37)
<223> OTHER INFORMATION: His, Arg, Lys, or absent

<400> SEQUENCE: 10

Xaa Xaa His Ala Asp Gly Ser Phe Ser Asp Glu Met Asn Thr Ile Leu
1               5                   10                  15

Asp Asn Leu Ala Xaa Arg Asp Phe Ile Asn Trp Leu Ile Gln Thr Lys
            20                  25                  30

Ile Thr Asp Xaa Xaa
            35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 11
```

His Gly Glu Gly Thr Phe Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 12
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 12

His Gly Glu Gly Thr Phe Ser Asp Glu Leu Ala Thr Ile Leu Asp Ala
1               5                   10                  15

Leu Ala Ala Arg Ile Phe Ile Ala Trp Leu Ile Ala Thr Lys Lys Lys
            20                  25                  30

Lys Lys Lys
        35

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 13

His Gly Asp Gly Ser Pro Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 14

His Gly Glu Gly Ser Phe Ser Asp Glu Leu Ala Thr Ile Leu Asp Asn
1               5                   10                  15

Leu Ala Ala Arg Asp Phe Ile Ala Trp Leu Ile Gln Thr Lys Ile Thr
            20                  25                  30

Asp

<210> SEQ ID NO 15
<211> LENGTH: 33
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 15

His Gly Asp Gly Ser Phe Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 16

His Gly Asp Gly Ser Phe Ser Asp Glu Leu Ala Thr Ile Leu Asp Asn
1               5                   10                  15

Leu Ala Ala Arg Asp Phe Ile Ala Trp Leu Ile Ala Thr Lys Ile Thr
            20                  25                  30

Asp

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 17

His Gly Glu Gly Ser Phe Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 18

His Gly Asp Gly Ser Phe Ser Ser Glu Leu Ala Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35
```

```
<210> SEQ ID NO 19
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 19

His Gly Asp Gly Ser Phe Ser Asp Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 20

His Gly Asp Gly Ser Phe Thr Ser Glu Leu Ala Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 21

His Gly Asp Gly Ser Phe Ser Asp Glu Leu Lys Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 22
```

```
His Gly Asp Gly Ser Phe Thr Asp Glu Leu Lys Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 23

His Gly Asp Gly Ser Phe Thr Ser Glu Leu Lys Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 24

His Gly Asp Gly Ser Phe Thr Asp Glu Leu Ala Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 25

His Gly Asp Gly Ser Phe Ser Ser Glu Leu Ala Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 26
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<223> OTHER INFORMATION: GLP-2 analogue

<400> SEQUENCE: 26

His Gly Asp Gly Ser Phe Ser Asp Glu Leu Asn Thr Ile Leu Asp Asn
1               5                   10                  15

Leu Ala Ala Arg Asp Phe Ile Ala Trp Leu Ile Gln Thr Lys Ile Thr
            20                  25                  30

Asp Lys Lys Lys Lys Lys Lys
        35

<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 27

His Gly Asp Gly Ser Phe Thr Asp Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 28
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 28

His Gly Asp Gly Ser Phe Thr Ser Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 29
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 29

His Gly Asp Gly Ser Phe Ser Ser Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30
```

Lys Lys Lys
         35

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 30

His Gly Asp Gly Ser Phe Ser Asp Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 31

His Gly Asp Gly Ser Phe Thr Asp Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 32

His Gly Asp Gly Ser Phe Thr Ser Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 33

His Gly Asp Gly Ser Phe Ser Ser Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 34

His Gly Asp Gly Ser Phe Thr Ser Glu Leu Ala Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 35

His Gly Asp Gly Ser Phe Ser Asp Glu Leu Lys Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 36

His Gly Asp Gly Ser Phe Thr Asp Glu Leu Lys Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 37

His Gly Asp Gly Ser Phe Ser Asp Glu Leu Ala Thr Ile Leu Asp Asn
1               5                   10                  15

Leu Ala Ala Arg Asp Phe Ile Ala Trp Leu Ile Gln Thr Lys Ile Thr
            20                  25                  30

Asp Lys Lys Lys Lys Lys Lys
        35

```
<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 38

His Gly Asp Gly Ser Phe Ser Asp Glu Leu Ala Thr Ile Leu Asp Asn
1               5                   10                  15

Leu Ala Ala Arg Asp Phe Ile Ala Trp Leu Ile Gln Thr Lys Ile Thr
            20                  25                  30

Asp

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 39

His Gly Asp Gly Ser Phe Ser Asp Glu Leu Ala Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 40

His Gly Asp Gly Ser Phe Thr Ser Glu Leu Lys Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 41

His Gly Asp Gly Ser Phe Thr Asp Glu Leu Ala Thr Ile Leu Asp Asn
1               5                   10                  15

Leu Ala Ala Arg Asp Phe Ile Ala Trp Leu Ile Gln Thr Lys
            20                  25                  30
```

```
<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 42

His Gly Glu Gly Thr Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 43
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 43

His Gly Glu Gly Thr Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 44
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 44

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 45
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 45

His Gly Glu Gly Ser Phe Ser Asp Glu Leu Ser Thr Ile Leu Asp Ala
```

```
1               5                   10                  15
Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 46
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 46

His Gly Glu Gly Thr Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 47
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 47

His Gly Glu Gly Ser Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 48
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 48

His Gly Glu Gly Ser Phe Ser Asp Glu Leu Lys Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 49
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 49

His Gly Glu Gly Thr Phe Ser Asp Glu Leu Lys Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 50

His Gly Glu Gly Thr Phe Ser Ser Glu Leu Lys Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 51

His Gly Glu Gly Thr Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 52
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 52

His Gly Glu Gly Thr Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30
```

Asp

<210> SEQ ID NO 53
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 53

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 54

His Gly Glu Gly Ser Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 55

His Gly Glu Gly Thr Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 56
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 56

His Gly Glu Gly Ser Phe Ser Ser Glu Leu Ala Thr Ile Leu Asp Ala

-continued

```
                1               5                  10                  15
Leu Ala Ala Arg Asp Phe Ile Ala Trp Leu Ile Ala Thr Lys Ile Thr
                20                  25                  30

Asp

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 57

His Gly Glu Gly Ser Phe Ser Asp Glu Leu Lys Thr Ile Leu Asp Ala
1               5                  10                  15

Leu Ala Ala Arg Asp Phe Ile Ala Trp Leu Ile Ala Thr Lys Ile Thr
                20                  25                  30

Asp

<210> SEQ ID NO 58
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 58

His Gly Glu Gly Thr Phe Ser Asp Glu Leu Lys Thr Ile Leu Asp Ala
1               5                  10                  15

Leu Ala Ala Arg Asp Phe Ile Ala Trp Leu Ile Ala Thr Lys Ile Thr
                20                  25                  30

Asp

<210> SEQ ID NO 59
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue

<400> SEQUENCE: 59

His Gly Glu Gly Thr Phe Ser Ser Glu Leu Lys Thr Ile Leu Asp Ala
1               5                  10                  15

Leu Ala Ala Arg Asp Phe Ile Ala Trp Leu Ile Ala Thr Lys Ile Thr
                20                  25                  30

Asp

<210> SEQ ID NO 60
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<223> OTHER INFORMATION: GLP-2 analogue
<220> FEATURE:
<221> NAME/KEY: MOD_RES
<222> LOCATION: (1)..(20)
<223> OTHER INFORMATION: Ala, Leu, Ser, Thr, Tyr, Asn, Gln, Asp, Glu,
      Lys, Arg, His, Met, Orn, or absent
<220> FEATURE:
<221> NAME/KEY: MOD_RES
<222> LOCATION: (22)..(22)
<223> OTHER INFORMATION: Gly, Ala or Sar
<220> FEATURE:
<221> NAME/KEY: MOD_RES
<222> LOCATION: (23)..(23)
<223> OTHER INFORMATION: Glu or Asp
<220> FEATURE:
<221> NAME/KEY: MOD_RES
<222> LOCATION: (25)..(25)
<223> OTHER INFORMATION: Ser or Thr
<220> FEATURE:
<221> NAME/KEY: MOD_RES
<222> LOCATION: (26)..(26)
<223> OTHER INFORMATION: Phe or Pro
<220> FEATURE:
<221> NAME/KEY: MOD_RES
<222> LOCATION: (27)..(27)
<223> OTHER INFORMATION: Ser or Thr
<220> FEATURE:
<221> NAME/KEY: MOD_RES
<222> LOCATION: (28)..(28)
<223> OTHER INFORMATION: Asp or Ser
<220> FEATURE:
<221> NAME/KEY: MOD_RES
<222> LOCATION: (29)..(29)
<223> OTHER INFORMATION: Glu or Asp
<220> FEATURE:
<221> NAME/KEY: MOD_RES
<222> LOCATION: (30)..(30)
<223> OTHER INFORMATION: Met, Leu, Nle, or an oxidatively stable
      Met-replacement amino acid
<220> FEATURE:
<221> NAME/KEY: MOD_RES
<222> LOCATION: (31)..(31)
<223> OTHER INFORMATION: Asn, Ala, Lys, or Ser
<220> FEATURE:
<221> NAME/KEY: MOD_RES
<222> LOCATION: (32)..(32)
<223> OTHER INFORMATION: Thr or Lys
<220> FEATURE:
<221> NAME/KEY: MOD_RES
<222> LOCATION: (33)..(33)
<223> OTHER INFORMATION: Ile, Glu or Gln
<220> FEATURE:
<221> NAME/KEY: MOD_RES
<222> LOCATION: (34)..(34)
<223> OTHER INFORMATION: Leu, Met, or Nle
<220> FEATURE:
<221> NAME/KEY: MOD_RES
<222> LOCATION: (35)..(35)
<223> OTHER INFORMATION: Asp or Glu
<220> FEATURE:
<221> NAME/KEY: MOD_RES
<222> LOCATION: (36)..(36)
<223> OTHER INFORMATION: Asn or Ala
<220> FEATURE:
<221> NAME/KEY: MOD_RES
<222> LOCATION: (37)..(37)
<223> OTHER INFORMATION: Leu or Glu
<220> FEATURE:
<221> NAME/KEY: MOD_RES
<222> LOCATION: (38)..(38)
<223> OTHER INFORMATION: Ala or Aib
<220> FEATURE:
<221> NAME/KEY: MOD_RES
<222> LOCATION: (39)..(39)
<223> OTHER INFORMATION: Ala or Thr
<220> FEATURE:
<221> NAME/KEY: MOD_RES
<222> LOCATION: (40)..(40)
<223> OTHER INFORMATION: Arg or Lys
```

-continued

```
<220> FEATURE:
<221> NAME/KEY: MOD_RES
<222> LOCATION: (41)..(41)
<223> OTHER INFORMATION: Asp or Ile
<220> FEATURE:
<221> NAME/KEY: MOD_RES
<222> LOCATION: (44)..(44)
<223> OTHER INFORMATION: Asn, Ala, or Glu
<220> FEATURE:
<221> NAME/KEY: MOD_RES
<222> LOCATION: (48)..(48)
<223> OTHER INFORMATION: Gln, Ala, or Asn
<220> FEATURE:
<221> NAME/KEY: MOD_RES
<222> LOCATION: (51)..(51)
<223> OTHER INFORMATION: Pro Ile, or absent
<220> FEATURE:
<221> NAME/KEY: MOD_RES
<222> LOCATION: (52)..(52)
<223> OTHER INFORMATION: Thr or absent
<220> FEATURE:
<221> NAME/KEY: MOD_RES
<222> LOCATION: (53)..(53)
<223> OTHER INFORMATION: Asp, Asn, or absent
<220> FEATURE:
<221> NAME/KEY: MOD_RES
<222> LOCATION: (54)..(73)
<223> OTHER INFORMATION: Ala, Leu, Ser, Thr, Tyr, Asn, Gln, Asp, Glu,
      Lys, Arg, His, Met, Orn, or absent

<400> SEQUENCE: 60

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa His Xaa Xaa Gly Xaa Xaa Xaa Xaa Xaa Xaa Xaa Xaa
            20                  25                  30

Xaa Xaa Xaa Xaa Xaa Xaa Xaa Xaa Xaa Phe Ile Xaa Trp Leu Ile Xaa
        35                  40                  45

Thr Lys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa
65                  70

<210> SEQ ID NO 61
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue
<220> FEATURE:
<221> NAME/KEY: MOD_RES
<222> LOCATION: (1)..(20)
<223> OTHER INFORMATION: Ala, Leu, Ser, Thr, Tyr, Asn, Gln, Asp, Glu,
      Lys, Arg, His, Met, Orn, or absent
<220> FEATURE:
<221> NAME/KEY: MOD_RES
<222> LOCATION: (23)..(23)
<223> OTHER INFORMATION: Glu or Asp
<220> FEATURE:
<221> NAME/KEY: MOD_RES
<222> LOCATION: (25)..(25)
<223> OTHER INFORMATION: Ser or Thr
<220> FEATURE:
<221> NAME/KEY: MOD_RES
<222> LOCATION: (27)..(27)
<223> OTHER INFORMATION: Ser or Thr
<220> FEATURE:
<221> NAME/KEY: MOD_RES
<222> LOCATION: (28)..(28)
<223> OTHER INFORMATION: Asp or Ser
<220> FEATURE:
```

```
<221> NAME/KEY: MOD_RES
<222> LOCATION: (29)..(29)
<223> OTHER INFORMATION: Glu or Asp
<220> FEATURE:
<221> NAME/KEY: MOD_RES
<222> LOCATION: (30)..(30)
<223> OTHER INFORMATION: Met, Leu, Nle, or an oxidatively stable
      Met-replacement amino acid
<220> FEATURE:
<221> NAME/KEY: MOD_RES
<222> LOCATION: (31)..(31)
<223> OTHER INFORMATION: Asn, Ala, Lys or Ser
<220> FEATURE:
<221> NAME/KEY: MOD_RES
<222> LOCATION: (32)..(32)
<223> OTHER INFORMATION: Thr or Lys
<220> FEATURE:
<221> NAME/KEY: MOD_RES
<222> LOCATION: (33)..(33)
<223> OTHER INFORMATION: Ile, Glu, or Gln
<220> FEATURE:
<221> NAME/KEY: MOD_RES
<222> LOCATION: (34)..(34)
<223> OTHER INFORMATION: Leu, Met or Nle
<220> FEATURE:
<221> NAME/KEY: MOD_RES
<222> LOCATION: (35)..(35)
<223> OTHER INFORMATION: Asp or Glu
<220> FEATURE:
<221> NAME/KEY: MOD_RES
<222> LOCATION: (36)..(36)
<223> OTHER INFORMATION: Asn or Ala
<220> FEATURE:
<221> NAME/KEY: MOD_RES
<222> LOCATION: (37)..(37)
<223> OTHER INFORMATION: Leu or Glu
<220> FEATURE:
<221> NAME/KEY: MOD_RES
<222> LOCATION: (39)..(39)
<223> OTHER INFORMATION: Ala or Thr
<220> FEATURE:
<221> NAME/KEY: MOD_RES
<222> LOCATION: (44)..(44)
<223> OTHER INFORMATION: Asn or Ala
<220> FEATURE:
<221> NAME/KEY: MOD_RES
<222> LOCATION: (48)..(48)
<223> OTHER INFORMATION: Gln, Ala, or Asn
<220> FEATURE:
<221> NAME/KEY: MOD_RES
<222> LOCATION: (51)..(51)
<223> OTHER INFORMATION: Pro, Ile, or absent
<220> FEATURE:
<221> NAME/KEY: MOD_RES
<222> LOCATION: (52)..(52)
<223> OTHER INFORMATION: Thr or absent
<220> FEATURE:
<221> NAME/KEY: MOD_RES
<222> LOCATION: (53)..(53)
<223> OTHER INFORMATION: Asp or absent
<220> FEATURE:
<221> NAME/KEY: MOD_RES
<222> LOCATION: (54)..(73)
<223> OTHER INFORMATION: Ala, Leu, Ser, Thr, Tyr, Asn, Gln, Asp, Glu,
      Lys, Arg, His, Met, Orn, or absent

<400> SEQUENCE: 61

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa His Gly Xaa Gly Xaa Phe Xaa Xaa Xaa Xaa Xaa
            20                  25                  30

Xaa Xaa Xaa Xaa Xaa Ala Xaa Arg Asp Phe Ile Xaa Trp Leu Ile Xaa
        35                  40                  45

Thr Lys Xaa Xaa Xaa Xaa Xaa Xaa Xaa Xaa Xaa Xaa Xaa Xaa Xaa Xaa
    50                  55                  60
```

Xaa Xaa Xaa Xaa Xaa Xaa Xaa Xaa Xaa
65                  70

<210> SEQ ID NO 62
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLP-2 analogue
<220> FEATURE:
<221> NAME/KEY: MOD_RES
<222> LOCATION: (1)..(20)
<223> OTHER INFORMATION: Ala, Leu, Ser, Thr, Tyr, Asn, Gln, Asp, Glu,
      Lys, Arg, His, Met, Orn, or absent
<220> FEATURE:
<221> NAME/KEY: MOD_RES
<222> LOCATION: (23)..(23)
<223> OTHER INFORMATION: Glu or Asp
<220> FEATURE:
<221> NAME/KEY: MOD_RES
<222> LOCATION: (25)..(25)
<223> OTHER INFORMATION: Ser or Thr
<220> FEATURE:
<221> NAME/KEY: MOD_RES
<222> LOCATION: (27)..(27)
<223> OTHER INFORMATION: Ser or Thr
<220> FEATURE:
<221> NAME/KEY: MOD_RES
<222> LOCATION: (28)..(28)
<223> OTHER INFORMATION: Asp or Ser
<220> FEATURE:
<221> NAME/KEY: MOD_RES
<222> LOCATION: (30)..(30)
<223> OTHER INFORMATION: Met, Leu, Nle, or an oxidatively stable
      Met-replacement amino acid
<220> FEATURE:
<221> NAME/KEY: MOD_RES
<222> LOCATION: (31)..(31)
<223> OTHER INFORMATION: Asn, Ala, Lys, or Ser
<220> FEATURE:
<221> NAME/KEY: MOD_RES
<222> LOCATION: (36)..(36)
<223> OTHER INFORMATION: Asn or Ala
<220> FEATURE:
<221> NAME/KEY: MOD_RES
<222> LOCATION: (44)..(44)
<223> OTHER INFORMATION: Asn or Ala
<220> FEATURE:
<221> NAME/KEY: MOD_RES
<222> LOCATION: (48)..(48)
<223> OTHER INFORMATION: Gln or Ala
<220> FEATURE:
<221> NAME/KEY: MOD_RES
<222> LOCATION: (51)..(51)
<223> OTHER INFORMATION: Pro or absent
<220> FEATURE:
<221> NAME/KEY: MOD_RES
<222> LOCATION: (52)..(52)
<223> OTHER INFORMATION: Thr or absent
<220> FEATURE:
<221> NAME/KEY: MOD_RES
<222> LOCATION: (53)..(53)
<223> OTHER INFORMATION: Asp or absent
<220> FEATURE:
<221> NAME/KEY: MOD_RES
<222> LOCATION: (54)..(73)
<223> OTHER INFORMATION: Ala, Leu, Ser, Thr, Tyr, Asn, Gln, Asp, Glu,
      Lys, Arg, His, Met, Orn, or absent

<400> SEQUENCE: 62

Xaa Xaa Xaa Xaa Xaa Xaa Xaa Xaa Xaa Xaa Xaa Xaa Xaa Xaa Xaa Xaa
1               5                   10                  15

```
Xaa Xaa Xaa Xaa His Gly Xaa Gly Xaa Phe Xaa Xaa Glu Xaa Xaa Thr
            20              25              30

Ile Leu Asp Xaa Leu Ala Ala Arg Asp Phe Ile Xaa Trp Leu Ile Xaa
        35              40              45

Thr Lys Xaa Xaa Xaa Xaa Xaa Xaa Xaa Xaa Xaa Xaa Xaa Xaa Xaa Xaa
    50              55              60

Xaa Xaa Xaa Xaa Xaa Xaa Xaa Xaa Xaa
65                  70

<210> SEQ ID NO 63
<211> LENGTH: 34
<212> TYPE: PRT
<213> ORGANISM: Homo sapiens

<400> SEQUENCE: 63

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg
```

TREATMENT OF LOWER URINARY TRACT EPITHELIUM WITH GLUCAGON LIKE PEPTIDE 2

RELATED APPLICATIONS

This application is a continuation of U.S. application Ser. No. 16/488,628, filed Aug. 26, 2019, which is a U.S. national phase application under U.S.C. 371 of PCT International Application No. PCT/US2018/019949, filed Feb. 27, 2018, which claims benefit of and priority to U.S. Provisional Application No. 62/463,923, filed Feb. 27, 2017, the entirety of each of which is incorporated herein by reference in its entirety for all purposes.

FIELD

The present invention relates to disorders of the lower urinary tract epithelium, and in particular, treatment of hemorrhagic cystitis, interstitial cystitis/bladder pain syndrome, overactive bladder, and bladder wall lesions in vivo, including Hunner's lesions. In particular, the present invention relates to treatment formulations comprising glucagon like peptide 2 (GLP-2) and methods for treatment of hemorrhagic cystitis, interstitial cystitis/bladder pain syndrome, and bladder wall lesions, including Hunner's lesions in patients.

BACKGROUND

Cystitis is a disorder of the lower urinary tract that causes urinary urgency and frequency and/or pelvic pain. Cystitis can result from bacterial and viral infections (UTI's), interstitial cystitis/bladder pain syndrome or induced chemically or by radiation therapy. In the most severe form hemorrhagic cystitis, can include dysuria, hematuria and hemorrhage. Hemorrhagic cystitis is usually the result of chemotherapy and radiation therapy or the most severe form of IC presenting as Hunner's lesions forming on the wall of the bladder, occurring in 5 to 10 percent of patients who have IC. Overactive bladder (OAB) is a disease similar to IC, except patients do not experience pain.

SUMMARY

In an aspect, a method for treating a subject afflicted by a disorder of the subject's lower urinary tract epithelium is presented, wherein the disorder is characterized by damage to epithelial cells in the subject's lower urinary tract epithelium, the method comprising administering a therapeutically effective amount of at least one of GLP-2, a GLP-2 derivative, and a GLP-2 analog to the subject, wherein the therapeutically effective amount of the at least one of GLP-2, a GLP-2 derivative, and a GLP-2 analog is sufficient to promote proliferation of the epithelial cells in the subject's lower urinary tract epithelium, thereby treating the subject. The at least one of GLP-2, a GLP-2 derivative, and a GLP-2 analog may be administered in a composition which comprises a pharmaceutically acceptable carrier or the like.

In an embodiment thereof, the disorder of the lower urinary tract epithelium comprises at least one of hemorrhagic cystitis, interstitial cystitis/bladder pain syndrome, and overactive bladder. In a more particular embodiment, the interstitial cystitis/bladder pain syndrome comprises Hunner's lesions.

In another aspect, a method for promoting regeneration of urothelium in a subject is presented, wherein the urothelium is characterized by damage to epithelial cells in the subject's uroepithelium, the method comprising administering a therapeutically effective amount of at least one of GLP-2, a GLP-2 derivative, and a GLP-2 analog to the subject, wherein the therapeutically effective amount of the at least one of GLP-2, a GLP-2 derivative, and a GLP-2 analog is sufficient to promote proliferation of the epithelial cells in the subject's uroepithelium, thereby promoting regeneration of urothelium in a subject. The at least one of GLP-2, a GLP-2 derivative, and a GLP-2 analog may be administered in a composition which comprises a pharmaceutically acceptable carrier or the like.

In an embodiment thereof, the damage to epithelial cells in the subject's uroepithelium is associated with at least one of hemorrhagic cystitis, interstitial cystitis/bladder pain syndrome, and overactive bladder. In a more particular embodiment, the interstitial cystitis/bladder pain syndrome comprises Hunner's lesions.

In an embodiment thereof, the subject is a mammal. In a more particular embodiment, the mammal is a human.

As described herein, a method for treating a subject afflicted by a disorder of the subject's lower urinary tract epithelium or a method for promoting regeneration of urothelium in a subject may be assessed based on at least one of the following: reduction in hematuria or hemorrhage, reduction of visible bladder lesions, reduction of pain, reduction of urinary frequency, reduction of urinary urgency, reduction of requirement for narcotic administration, reduction of incontinence, and reduction of abnormal permeability of the urothelium to potassium.

In a particular embodiment, the at least one of GLP-2, a GLP-2 derivative, and a GLP-2 analog comprises at least one of SEQ ID NOs: 1-3 and 6-62. In a more particular embodiment, the at least one of GLP-2, a GLP-2 derivative, and a GLP-2 analog comprises at least one of SEQ ID NO: 1, SEQ ID NO: 2, SEQ ID NO: 8, SEQ ID NOs: 11-59, and SEQ ID NO: 63. In a still more particular embodiment, the at least one of GLP-2, a GLP-2 derivative, and a GLP-2 analog comprises at least one of SEQ ID NO: 1 and SEQ ID NO: 2.

In another particular embodiment, the at least one of GLP-2, a GLP-2 derivative, and a GLP-2 analog is administered intravesicularly, intralesionally, orally, intravenously, intraperitoneally, intramuscularly, subcutaneously, intradermally, rectally, nasally, topically, or by inhalation via nebulizer or inhaler to the subject. In yet another particular embodiment, the at least one of GLP-2, a GLP-2 derivative, and a GLP-2 analog is administered directly to the subject's lower urinary tract. In another particular embodiment, the at least one of GLP-2, a GLP-2 derivative, and a GLP-2 analog is administered directly to the subject's bladder. In an even more particular embodiment, the at least one of GLP-2, a GLP-2 derivative, and a GLP-2 analog is administered directly into the Hunner's lesions of the subject.

In another particular embodiment, the disorder of the subject's lower urinary tract epithelium is due to an injury comprising at least one of a chemical insult, mechanical insult, and disease. In a more particular embodiment, the disease is a urinary tract infection. In an even more particular embodiment, the subject is disease-free and the disorder of the subject's lower urinary tract epithelium is a secondary by product of the disease. In yet another particular embodiment, the disease causative of the injury is a cancer and the subject is determined to be cancer-free.

In another particular embodiment, the at least one of GLP-2, a GLP-2 derivative, and a GLP-2 analog is administered at a dose in a range of 10 µg/kg body weight/day to about 10 mg/kg/day. In yet another particular embodiment, the at least one of GLP-2, a GLP-2 derivative, and a GLP-2 analog is administered at a dose in a range of 50 µg/kg/day to about 5 mg/kg/day. In a further particular embodiment, the at least one of GLP-2, a GLP-2 derivative, and a GLP-2 analog is administered at a dose in a range of 100 µg/kg/day to 1 mg/kg/day.

In another particular embodiment, the at least one of GLP-2, a GLP-2 derivative, and a GLP-2 analog is administered in a localized fashion (e.g., intravesicularly) in a concentration range of 0.01 µM-2 µM. In yet another particular embodiment, the at least one of GLP-2, a GLP-2 derivative, and a GLP-2 analog is administered intravesicularly in a concentration range of 0.01 µM-1 µM. In yet another particular embodiment, the at least one of GLP-2, a GLP-2 derivative, and a GLP-2 analog is administered intravesicularly in a concentration of about 0.1 µM.

In particular embodiments of methods described herein, the at least one of GLP-2, a GLP-2 derivative, and a GLP-2 analog is administered once per 24 hour period, once per 48 hour period, once per 72 hour period, or once per week. In another particular embodiment, the at least one of GLP-2, a GLP-2 derivative, and a GLP-2 analog is administered intermittently to the subject in need thereof.

In another aspect, a method for treating a subject afflicted by at least one of interstitial cystitis/bladder pain syndrome and Hunner's lesions is presented, the method comprising administering a therapeutically effective amount of at least one of GLP-2, a GLP-2 derivative, and a GLP-2 analog to the subject; wherein the therapeutically effective amount of the at least one of GLP-2, a GLP-2 derivative, and a GLP-2 analog is sufficient to promote proliferation of epithelial cells in the subject's bladder, thereby treating the subject. The at least one of GLP-2, a GLP-2 derivative, and a GLP-2 analog may be administered in a composition which comprises a pharmaceutically acceptable carrier or the like. In an embodiment thereof, the subject is a mammal. In a more particular embodiment, the mammal is a human.

As described herein, a method for treating a subject afflicted by at least one of interstitial cystitis/bladder pain syndrome and Hunner's lesions may be assessed based on at least one of the following: reduction in hematuria or hemorrhage, reduction of visible bladder lesions, reduction of pain, reduction of urinary frequency, reduction of urinary urgency, reduction of requirement for narcotic administration, reduction of incontinence, and reduction of abnormal permeability of the urothelium to potassium.

In a particular embodiment, the at least one of GLP-2, a GLP-2 derivative, and a GLP-2 analog comprises at least one of SEQ ID NOs: 1-3 and 6-62. In a more particular embodiment, the at least one of GLP-2, a GLP-2 derivative, and a GLP-2 analog comprises at least one of SEQ ID NO: 1, SEQ ID NO: 2, SEQ ID NO: 8, SEQ ID NOs: 11-59, and SEQ ID NO: 63. In a still more particular embodiment, the at least one of GLP-2, a GLP-2 derivative, and a GLP-2 analog comprises at least one of SEQ ID NO: 1 and SEQ ID NO: 2.

In another particular embodiment, the at least one of GLP-2, a GLP-2 derivative, and a GLP-2 analog is administered intravesicularly, intralesionally, orally, intravenously, intraperitoneally, intramuscularly, subcutaneously, intradermally, rectally, nasally, topically, or by inhalation via nebulizer or inhaler to the subject. In yet another particular embodiment, the at least one of GLP-2, a GLP-2 derivative, and a GLP-2 analog is administered directly to the subject's lower urinary tract. In another particular embodiment, the at least one of GLP-2, a GLP-2 derivative, and a GLP-2 analog is administered directly to the subject's bladder. In an even more particular embodiment, the at least one of GLP-2, a GLP-2 derivative, and a GLP-2 analog is administered directly into the Hunner's lesions of the subject.

In another particular embodiment, the at least one of GLP-2, a GLP-2 derivative, and a GLP-2 analog is administered at a dose in a range of 10 µg/kg body weight/day to about 10 mg/kg/day. In yet another particular embodiment, the at least one of GLP-2, a GLP-2 derivative, and a GLP-2 analog is administered at a dose in a range of 50 µg/kg/day to about 5 mg/kg/day. In a further particular embodiment, the at least one of GLP-2, a GLP-2 derivative, and a GLP-2 analog is administered at a dose in a range of 100 µg/kg/day to 1 mg/kg/day.

In another particular embodiment, the at least one of GLP-2, a GLP-2 derivative, and a GLP-2 analog is administered in a localized fashion (e.g., intravesicularly) in a concentration range of 0.01 µM-2 µM. In yet another particular embodiment, the at least one of GLP-2, a GLP-2 derivative, and a GLP-2 analog is administered intravesicularly in a concentration range of 0.01 µM-1 µM. In yet another particular embodiment, the at least one of GLP-2, a GLP-2 derivative, and a GLP-2 analog is administered intravesicularly in a concentration of about 0.1 µM.

In a particular embodiment, the at least one of GLP-2, a GLP-2 derivative, and a GLP-2 analog is administered once per 24 hour period, once per 48 hour period, once per 72 hour period, or once per week. In another particular embodiment, the at least one of GLP-2, a GLP-2 derivative, and a GLP-2 analog is administered intermittently to the subject in need thereof.

In an embodiment of any one of the methods described herein, the at least one of GLP-2, a GLP-2 derivative, and a GLP-2 analog is administered once per 24 hour period, once per 48 hour period, once per 72 hour period, or once per week. Any one of the methods described herein may further comprise administering at least one additional therapeutic agent, wherein the at least one additional therapeutic agent comprises at least one of an anti-microbial agent (e.g., an antibiotic), a heparanoid (administered intravesicularly or systemically), a topical anesthetic (administered intravesicularly), an anti-inflammatory agent (administered systemically or locally), a systemic analgesic and an inhibitor of neuropathic pain, such as, e.g., gabapentanoids.

In another embodiment, use of at least one of GLP-2, a GLP-2 derivative, and a GLP-2 analog for treating a disorder of the lower urinary tract epithelium is described, comprising administering the at least one of GLP-2, a GLP-2 derivative, and a GLP-2 analog in a therapeutically effective amount sufficient to promote proliferation of epithelial cells in the lower urinary tract epithelium, thereby treating the disorder. The at least one of GLP-2, a GLP-2 derivative, and a GLP-2 analog may be administered in a composition which comprises a pharmaceutically acceptable carrier or the like.

In another embodiment, use of at least one of GLP-2, a GLP-2 derivative, and a GLP-2 analog for treating at least one of interstitial cystitis/bladder pain syndrome and Hunner's lesions is described, comprising administering the at least one of GLP-2, a GLP-2 derivative, and a GLP-2 analog in a therapeutically effective amount sufficient to promote proliferation of epithelial cells in the bladder, thereby treating the at least one of interstitial cystitis/bladder pain syndrome and the bladder wall lesions. The at least one of GLP-2, a GLP-2 derivative, and a GLP-2 analog may be administered in a composition which comprises a pharmaceutically acceptable carrier or the like.

In another embodiment, use of at least one of GLP-2, a GLP-2 derivative, and a GLP-2 analog for promoting regeneration of urothelium is described, comprising administering the at least one of GLP-2, a GLP-2 derivative, and a GLP-2 analog in a therapeutically effective amount sufficient to promote proliferation of epithelial cells in the urothelium, thereby promoting regeneration of the urothelium. The at least one of GLP-2, a GLP-2 derivative, and a GLP-2 analog may be administered in a composition which comprises a pharmaceutically acceptable carrier or the like.

In some embodiments, the present invention is a method, comprising:
contacting a bladder epithelial cell with an effective amount of a glucagon like peptide 2 (GLP-2) receptor agonist to result in the bladder epithelial cell divison rate increasing within 24 to 72 hours, wherein the increased divison rate is between 10 and 100% compared to an untreated bladder epithelial cell.

In some embodiments, the GLP-2 receptor agonist comprises HADGSFSDEMNTILDNLAARDFINWLIQTKITD (SEQ ID NO: 1). In some embodiments, the GLP-2 receptor agonist comprises HGDGSFSDEMNTILDNLAARDFINWLIQTKITD (SEQ ID NO: 2). In some embodiments, the GLP-2 receptor agonist comprises an amino terminal aceylated, carboxy terminal amidated, pegylated, or glycosylated SEQ ID NO: 1 or SEQ ID NO: 2.

In some embodiments, the effective amount of the GLP-2 receptor agonist is between $1\times10^{-11}$ and $1\times10^{-7}$ mol/L.

In some embodiments, the present invention is a method, comprising:
administering an effective amount of a GLP-2 receptor agonist for a sufficient period of time so as to result in treating or ameliorating a lower urinary tract disorder.

In some embodiments, the disorder of the lower urinary tract is selected from the group consisting of: bacterial cystitis, fungal cystitis, urethral syndrome, chronic pelvic pain syndrome, radiation-induced cystitis, chemotherapy-induced cystitis, chemically-induced cystitis (due, e.g., to use of the narcotic ketamine) interstitial cystitis/bladder pain syndrome, overactive bladder, hemorrhagic cystitis, and Hunner's lesions.

In some embodiments, the GLP-2 receptor agonist is administered intravesicularly.

In some embodiments, the effective amount of a GLP-2 receptor agonist is between $1\times10^{-11}$ and $1\times10^{-7}$ mol/L. In other embodiments, the effective amount of a GLP-2 receptor agonist is between $1\times10^{-8}$ to $1\times10^{-5}$ mol/L. In further embodiments, the effective amount of a GLP-2 receptor agonist is between $2.3\times10^{-7}$ to $4.7\times10^{-7}$ mol/L. In still further embodiments, the effective amount of a GLP-2 receptor agonist is between $1\times10^{-7}$ to $5\times10^{-5}$ mol/L. Accordingly, the effective amount of a GLP-2 receptor agonist may be between $1\times10^{-11}$ to $5\times10^{-5}$ mol/L In some embodiments, the hemorrhagic cystitis is induced by radiation.

In some embodiments, the hemorrhagic cystitis is induced by chemotherapy.

In some embodiments, the present invention is a composition comprising a GLP-2 receptor agonist for treating or ameliorating a disorder of the lower urinary tract.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION

Figure 1:
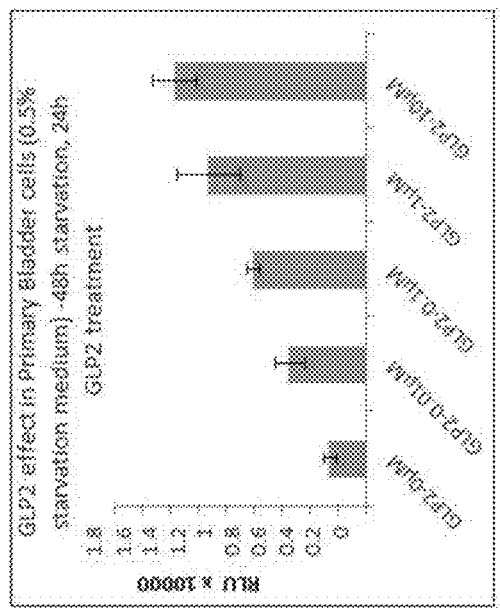
FIG. 1 presents a histogram plot depicting results from a BrdU cell proliferation assay. Primary human bladder epithelial cells were nutrient starved as indicated and treated with GLP-2 for 24 hours at the indicated concentrations
Figure 1:
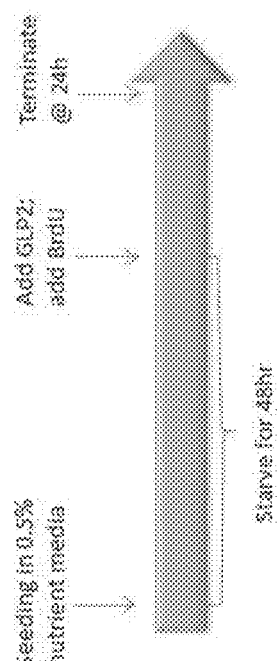

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

For clarity of disclosure, and not by way of limitation, the detailed description of the invention is divided into the following subsections that describe or illustrate certain features, embodiments or applications of the present invention.

Throughout the description, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the present invention is a method, comprising:
contacting a bladder epithelial cell with an effective amount of a glucagon like peptide 2 (GLP-2) receptor agonist to result in the bladder epithelial cell division rate increasing within 24 to 72 hours, wherein the increased division rate is between 10 and 100% compared to an untreated bladder epithelial cell.

In some embodiments, the GLP-2 receptor agonist comprises HADGSFSDEMNTILDNLAARDFINWLIQTKITD (SEQ ID NO. 1). In some embodiments, the GLP-2 receptor agonist comprises HGDGSFSDEMNTILDNLAARDFINWLIQTKITD (SEQ ID NO: 2). In some embodiments, the GLP-2 receptor agonist comprises an amino terminal aceylated, carboxy terminal amidated, pegylated, or glycolsylated SEQ ID NO: 1 or SEQ ID NO: 2. In some embodiments, the effective amount of the GLP-2 receptor agonist is between $1\times10^{-11}$ and $1\times10^{-7}$ mol/L.

In some embodiments, the increased divison rate of the contacted bladder epithelial cell is between 10 and 100% compared to an untreated bladder epithelial cell. In some embodiments, the increased divison rate of the contacted bladder epithelial cell is between 20 and 100% compared to an untreated bladder epithelial cell. In some embodiments, the increased divison rate of the contacted bladder epithelial cell is between 30 and 100% compared to an untreated bladder epithelial cell. In some embodiments, the increased divison rate of the contacted bladder epithelial cell is between 40 and 100% compared to an untreated bladder epithelial cell. In some embodiments, the increased divison rate of the contacted bladder epithelial cell is between 50 and 100% compared to an untreated bladder epithelial cell. In some embodiments, the increased divison rate of the contacted bladder epithelial cell is between 60 and 100% compared to an untreated bladder epithelial cell. In some embodiments, the increased divison rate of the contacted bladder epithelial cell is between 70 and 100% compared to an untreated bladder epithelial cell. In some embodiments, the increased divison rate of the contacted bladder epithelial cell is between 80 and 100% compared to an untreated bladder epithelial cell. In some embodiments, the increased divison rate of the contacted bladder epithelial cell is between 90 and 100% compared to an untreated bladder epithelial cell.

In some embodiments, the increased divison rate of the contacted bladder epithelial cell is between 10 and 90% compared to an untreated bladder epithelial cell. In some embodiments, the increased divison rate of the contacted bladder epithelial cell is between 10 and 80% compared to an untreated bladder epithelial cell. In some embodiments, the increased divison rate of the contacted bladder epithelial cell is between 10 and 70% compared to an untreated bladder epithelial cell. In some embodiments, the increased divison rate of the contacted bladder epithelial cell is between 10 and 60% compared to an untreated bladder epithelial cell. In some embodiments, the increased divison rate of the contacted bladder epithelial cell is between 10 and 50% compared to an untreated bladder epithelial cell. In some embodiments, the increased divison rate of the contacted bladder epithelial cell is between 10 and 40% compared to an untreated bladder epithelial cell. In some embodiments, the increased divison rate of the contacted bladder epithelial cell is between 10 and 30% compared to an untreated bladder epithelial cell. In some embodiments, the increased divison rate of the contacted bladder epithelial cell is between 10 and 20% compared to an untreated bladder epithelial cell.

In some embodiments, the increased divison rate of the contacted bladder epithelial cell is between 20 and 90% compared to an untreated bladder epithelial cell. In some embodiments, the increased divison rate of the contacted bladder epithelial cell is between 30 and 80% compared to an untreated bladder epithelial cell. In some embodiments, the increased divison rate of the contacted bladder epithelial cell is between 40 and 70% compared to an untreated bladder epithelial cell. In some embodiments, the increased divison rate of the contacted bladder epithelial cell is between 50 and 60% compared to an untreated bladder epithelial cell.

In some embodiments, the present invention is a method, comprising:
    administering an effective amount of a GLP-2 receptor agonist for a sufficient period of time so as to result in treating or ameliorating a lower urinary tract disorder.
In some embodiments, the disorder of the lower urinary tract is selected from the group consisting of: bacterial cystitis, fungal cystitis, urethral syndrome, chronic pelvic pain syndrome, radiation-induced cystitis, chemotherapy-induced cystitis, interstitial cystitis/bladder pain syndrome, overactive bladder, hemorrhagic cystitis, and Hunner's lesions.

In some embodiments, the GLP-2 receptor agonist is administered intravesicularly. In some embodiments, the effective amount is between $1\times10^{-11}$ and $1\times10^{-7}$ mol/L. In some embodiments, the hemorrhagic cystitis is induced by radiation. In some embodiments, the hemorrhagic cystitis is induced by chemotherapy.

In some embodiments, a composition comprising a GLP-2 receptor agonist for treating or ameliorating a disorder of the lower urinary tract in a subject in need thereof is presented. In some embodiments, the disorder of the lower urinary tract is bacterial cystitis, fungal cystitis, urethral syndrome, chronic pelvic pain syndrome, radiation-induced cystitis, chemotherapy-induced cystitis, interstitial cystitis/bladder pain syndrome, overactive bladder, hemorrhagic cystitis, or Hunner's lesions.

In other embodiments, a composition comprising a GLP-2 receptor agonist for preventing re-occurrence of a disorder of the lower urinary tract is presented. In embodiments thereof, the subject in need thereof is identified as at risk for a re-occurrence of a disorder of the lower urinary tract because they have been previously diagnosed as having the disorder and are being monitored (e.g., by a medical practitioner and/or by self-monitoring) for the re-appearance of symptoms of the disorder and/or the disorder is chronic and therefore, manifests repeatedly. Exemplary disorders that are chronic and/or tend to reappear include: chronic pelvic pain syndrome, radiation-induced cystitis, chemotherapy-induced cystitis, interstitial cystitis, overactive bladder, hemorrhagic cystitis, and Hunner's lesions.

As used herein, the terms "treat" or "ameliorate" refer to any detectable improvement, whether subjective or objective, in the lower urinary tract disorder of the subject (e.g., human patient) to whom the composition is administered. For example, the terms "treat" or "ameliorate" can refer to an improvement as determined by the PORTS scale [e.g., using the methods disclosed in CL Parsons, Benson G, Childs S J, Hanno P, Sant G R, and Webster G. "A quantitatively controlled method to study prospectively/bladder pain syndrome and demonstrate the efficacy of pentosanpolysulfate." J Urol, 1993. 150(3): p. 845-8; the entire content of which is incorporated herein by reference], the PUF scale [e.g., using the methods disclosed in Parsons C L, Dell J, Stanford E J et al: "Increased prevalence of interstitial cystitis: previously unrecognized urologic and gynecologic cases identified using a new symptom questionnaire and intravesical potassium sensitivity." Urology 2002; 60:573; the entire content of which is incorporated herein by reference], or any component of the PORIS and/or PUF scales; reduction in hematuria or hemorrhage, reduction of visible bladder lesions, reduction of pain [e.g., using the methods disclosed in Parsons C L, Zupkas P, Proctor J, Koziol J, Franklin A, Giesing D, Davis E., Lakin C M, Kahn B S, and Garner W J. "Alkalinized lidocaine and heparin provide immediate relief of pain and urgency in patients with interstitial cystitis." J Sex Med 2012; 9:207-212; the entire content of which is incorporated herein by reference]; reduction of urinary frequency; reduction of urinary urgency; reduction of requirement for narcotic administration (wherein the dosing is at least one less dose compared with patients not treated with a GLP-2 receptor antagonist); reduction of incontinence; reduction of abnormal permeability of the urothelium to potassium [e.g., using the methods disclosed in Parsons C L, Zupkas P, Parsons J K. "Intravesical potassium sensitivity in patients with interstitial cystitis/bladder pain syndrome and urethral syndrome." Urology. 2001 March; 57(3):428-32; discussion 432-3; the entire content of which is incorporated herein by reference]; or improvement in more than one of these parameters. The terms "treat" or "ameliorate" do not state or imply a cure for the underlying lower urinary tract disorder.

As used herein, the term "prevent" refers to a reduction in a subject's tendency (e.g., expected and/or pre-determined) to present with clinical symptoms of a disorder of the lower urinary tract following a previous bout of the disorder. In an embodiment wherein the disorder is chronic, compositions described herein may be administered prophylactically to manage the disorder on an ongoing basis. A reduction may refer to any detectable improvement in the frequency (reduction in frequency of recurrence) and/or duration (reduction in the length of time of a recurrence based on comparison to the duration of previous recurrence) of symptomatic presentation of the lower urinary tract disorder in the subject (e.g., human patient) to whom the composition is administered. The subject's expected and/or pre-determined tendency to present with clinical symptoms of a disorder of the lower urinary tract may be determined based on the subject's medical history and the nature and/or type of the condition (e.g., severity of previous bout, acute versus chronic bouts).

In some embodiments, the reduction in hematuria or hemorrhage is 10 to 100%. In some embodiments, the reduction in hematuria or hemorrhage is 10 to 90%. In some embodiments, the reduction in hematuria or hemorrhage is 10 to 80%. In some embodiments, the reduction in hematuria or hemorrhage is 10 to 70%. In some embodiments, the reduction in hematuria or hemorrhage is 10 to 60%. In some embodiments, the reduction in hematuria or hemorrhage is 10 to 50%. In some embodiments, the reduction in hematuria or hemorrhage is 10 to 40%. In some embodiments, the reduction in hematuria or hemorrhage is 10 to 30%. In some embodiments, the reduction in hematuria or hemorrhage is 10 to 20%.

In some embodiments, the reduction in hematuria or hemorrhage is 20 to 100%. In some embodiments, the reduction in hematuria or hemorrhage is 30 to 100%. In some embodiments, the reduction in hematuria or hemorrhage is 40 to 100%. In some embodiments, the reduction in hematuria or hemorrhage is 50 to 100%. In some embodiments, the reduction in hematuria or hemorrhage is 60 to 100%. In some embodiments, the reduction in hematuria or hemorrhage is 70 to 100%. In some embodiments, the reduction in hematuria or hemorrhage is 80 to 100%. In some embodiments, the reduction in hematuria or hemorrhage is 90 to 100%. In some embodiments, the reduction in hematuria or hemorrhage is 20 to 90%. In some embodiments, the reduction in hematuria or hemorrhage is 30 to 80%. In some embodiments, the reduction in hematuria or hemorrhage is 40 to 70%. In some embodiments, the reduction in hematuria or hemorrhage is 50 to 60%.

In some embodiments, the reduction of visible Hunner's lesions is 10 to 100%. In some embodiments, the reduction of visible Hunner's lesions is 10 to 90%. In some embodiments, the reduction of visible is 10 to 80%. In some embodiments, the reduction of visible Hunner's lesions is 10 to 70%. In some embodiments, the reduction of visible Hunner's lesions is 10 to 60%. In some embodiments, the reduction of visible Hunner's lesions is 10 to 50%. In some embodiments, the reduction of visible Hunner's lesions is 10 to 40%. In some embodiments, the reduction of visible Hunner's lesions is 10 to 30%. In some embodiments, the reduction of visible Hunner's lesions is 10 to 20%. The reduction of visible Hunner's lesions may be assessed by at least one of a decrease in the number of lesions and the size of particular lesions.

In some embodiments, the reduction of visible Hunner's lesions is 20 to 100%. In some embodiments, the reduction of visible Hunner's lesions is 30 to 100%. In some embodiments, the reduction of visible Hunner's lesions is 40 to 100%. In some embodiments, the reduction of visible Hunner's lesions is 50 to 100%. In some embodiments, the reduction of visible Hunner's lesions is 60 to 100%. In some embodiments, the reduction of visible Hunner's lesions is 70 to 100%. In some embodiments, the reduction of visible Hunner's lesions is 80 to 100%. In some embodiments, the reduction of visible Hunner's lesions is 90 to 100%. In some embodiments, the reduction of visible Hunner's lesions is 20 to 90%. In some embodiments, the reduction of visible Hunner's lesions is 30 to 80%. In some embodiments, the reduction of visible Hunner's lesions is 40 to 70%. In some embodiments, the reduction of visible Hunner's lesions is 50 to 60%. The reduction of visible Hunner's lesions may be assessed by at least one of a decrease in the number of lesions and the size of particular lesions.

The methods according to some embodiments of the present invention use methods for measuring pain as disclosed in Parsons C L, Zupkas P, Proctor J, Koziol J, Franklin A, Giesing D, Davis E, Lakin C M, Kahn B S, and Garner W J. "Alkalinized lidocaine and heparin provide immediate relief of pain and urgency in patients with interstitial cystitis." J Sex Med 2012; 9:207-212; the entire content of which is incorporated herein by reference. In some embodiments, the reduction of pain is 10 to 80%. In some embodiments, the reduction of pain is 10 to 70%. In some embodiments, the reduction of pain is 10 to 60%. In some embodiments, the reduction of pain is 10 to 50%. In some embodiments, the reduction of pain is 10 to 40%. In some embodiments, the reduction of pain is 10 to 30%. In some embodiments, the reduction of pain is 10 to 20%. In some embodiments, the reduction of pain is 20 to 80%. In some embodiments, the reduction of pain is 30 to 80%. In some embodiments, the reduction of pain is 40 to 80%. In some embodiments, the reduction of pain is 50 to 80%. In some embodiments, the reduction of pain is 60 to 80%. In some embodiments, the reduction of pain is 70 to 80%. In some embodiments, the reduction of pain is 20 to 70%. In some embodiments, the reduction of pain is 30 to 60%. In some embodiments, the reduction of pain is 40 to 50%.

In some embodiments, the reduction of urinary frequency is 10% to 90%. In some embodiments, the reduction of urinary frequency is 10% to 80%. In some embodiments, the reduction of urinary frequency is 10% to 70%. In some embodiments, the reduction of urinary frequency is 10% to 60%. In some embodiments, the reduction of urinary frequency is 10% to 50%. In some embodiments, the reduction of urinary frequency is 10% to 40%. In some embodiments, the reduction of urinary frequency is 10% to 30%. In some embodiments, the reduction of urinary frequency is 10% to 20%.

In some embodiments, the reduction of urinary frequency is 20% to 90%. In some embodiments, the reduction of urinary frequency is 30% to 90%. In some embodiments, the reduction of urinary frequency is 40% to 90%. In some embodiments, the reduction of urinary frequency is 50% to 90%. In some embodiments, the reduction of urinary frequency is 60% to 90%. In some embodiments, the reduction of urinary frequency is 70% to 90%. In some embodiments, the reduction of urinary frequency is 80% to 90%. In some embodiments, the reduction of urinary frequency is 30% to 80%. In some embodiments, the reduction of urinary frequency is 40% to 70%. In some embodiments, the reduction of urinary frequency is 50% to 60%.

In some embodiments, measuring urinary urgency can be performed using an 11 point visual analog scale as described in C. Parsons (2012) "Alkalinized lidocaine and heparin provide immediate relief of pain and urgency in patients with insterstitial cystitis" J. Sex Med (9) 207-212. In some embodiments, the reduction of urinary urgency is between 10 to 99%. In some embodiments, the reduction of urinary urgency is between 10 to 90%. In some embodiments, the reduction of urinary urgency is between 10 to 80%. In some embodiments, the reduction of urinary urgency is between 10 to 70%. In some embodiments, the reduction of urinary urgency is between 10 to 60%. In some embodiments, the reduction of urinary urgency is between 10 to 50%. In some embodiments, the reduction of urinary urgency is between 10 to 40%. In some embodiments, the reduction of urinary urgency is between 10 to 99%.

The term "urinary urgency" as used herein refers to a sudden and urgent sensation of a need to urinate. It is frequently, but not always, associated with interstitial cystitis/bladder pain syndrome, urinary incontinence, polyuria, and nocturia. Urinary urgency tends to increase in frequency with increasing age.

In one embodiment, the disorder of the lower urinary tract is selected from the group consisting of: inflammation of the bladder wall, bacterial cystitis, fungal cystitis, urethral syndrome, chronic pelvic pain syndrome, hemorrhagic cystitis, radiation-induced cystitis, chemotherapy-induced cystitis, interstitial cystitis/bladder pain syndrome, overactive bladder, and Hunner's lesions.

Without intending to be limited to any particular theory, hemorrhagic cystitis may be caused by chemotherapy, radiation therapy, or any combination thereof.

It is noteworthy that as of 2016 there were no effective therapies to treat radiation-induced cystitis. See, for example, Zwaans et al. (2016, Adv Radiation Oncol doi: 10.1016/j.adro.2016.07.004. Accordingly, there is an urgent need for new therapeutic regimens that address the needs of patients afflicted with this condition.

Glucagon Like Peptide 2 and Glucagon Like Peptide 2 Receptor

Glucagon Like Peptide 2 (GLP-2) is a 33 amino acid peptide with the amino acid sequence HADGSFSDEMNTILDNLAARDFINWLIQTKITD (SEQ ID NO. 1) co-produced by intestinal endocrine cells along with GLP-1 as the major proglucagon fragment and is released by proteolytic post-translational cleavage. GLP-2 promotes the growth of intestinal epithelium. GLP-1 and GLP-2 have short half lives in circulation (~3-7 minutes) due to a high rate of renal clearance and proteolytic cleavage by circulating Dipetidyl peptidase-4 (DPP4). The GLP-2 Receptor (GLP-2R), a G protein-coupled receptor superfamily member, is expressed in the gut and closely related to the glucagon receptor (GCGR) and the receptor for GLP1 (GLP1R). GLP-2R is 553aa protein and recognizes GLP-2 but not related members of the Glucagon peptide family. GLP-2 is understood by those skilled in the art to be a gut hormone that promotes highly specific growth and function of the intestinal epithelium. See, e.g., Austin et al. 2016, Current Opinion Pharmacology 31:13-18; the entire content of which is incorporated herein by reference. The characterized intestinal specific activity of GLP-2 is in keeping with the expression pattern of the GLP-2R. Even within the intestine, however, GLP-2R mRNA levels are extremely rare and GLP2R expression levels are low. See, e.g., Austin et al. (2016, supra).

In light of its gut specific activity and intestinal growth-promoting effects, GLP-2 and/or analogs/variants thereof have been used to treat a variety of gastrointestinal disorders in preclinical and clinical studies. A degradation-resistant (long acting) analog of GLP-2, teduglutide, has been approved for use in the treatment of short bowel syndrome (SBS) in human patients. Teduglutide has also been used to treat patients with moderately active Crohn's disease. Preclinical studies have also suggested that teduglutide could have therapeutic efficacy in the context of other gastrointestinal disorders, including enteritis due to the side-efects of various treatments, colitis, obesity-related and stress-related intestinal barrier dysfunction, and parenteral nutrition-induced gut atrophy. Further to the above, the GLP-2 analog elsiglutide has been used in clinical trials to evaluate its efficacy in the context of chemotherapy-induced diarrhea, but the results of a phase IIB study failed to reach statistical significance. See, e.g., Austin et al. (2016, supra) for a recent review of the above.

Further to the above, Thulesen et al. (2000, Peptides 21:1511-1517; the entire content of which is incorporated herein by reference) investigated GLP-2R expression by examining the distribution and binding of intravenously (iv) injected radiolabeled GLP-2 using autoradiography. Their study revealed that GLP-2 binds predominantly to the kidneys, liver, and gastrointestinal tract, and does not bind to the submandibular gland, lung, brain, heart, adipose tissue, skeletal muscle, uterus, ovary, urinary bladder, adrenal gland, thyroid gland, or skin. Given these results, one of skill in the art would not expect the submandibular gland, lung, brain, heart, adipose tissue, skeletal muscle, uterus, ovary, urinary bladder, adrenal gland, thyroid gland, or skin to express GLP-2R. The combined disclosures of Austin et al. (2016, supra) and Thulesen et al. (2000, supra), therefore, indicate that cellular response to GLP-2 is restricted to the gastrointestinal tract.

mRNA Levels are not Predictive of Protein Expression

It is generally understood that mRNA levels are frequently not predictive of protein expression levels encoded thereby. Further to this point, Edfors et al. (2016, Molecular Systems Biology 12:883; the entire content of which is incorporated herein by reference) disclose that transcript and protein levels do not correlate well unless a gene-specific RNA-to-protein (RTP) conversion factor independent of the tissue type is introduced. This position is corroborated by numerous other publications, including that of Bauernfeind et al. (2017, BMC Genomics 18:322; the entire content of which is incorporated herein by reference), which discloses that the correlation between transcript and protein expression is inconsistent.

One of skill in the art would also appreciate that cellular response to receptor agonist not only depends on the presence of agonist-binding receptors on the cell surface, but also depends on expression levels of those receptors. Agonist-binding receptors must be expressed in an amount sufficient to confer agonist responsiveness to a cell and the cell must have a functional intracellular signaling pathway downstream of the receptors to trigger an agonist receptor-mediated response.

Glucagon Like Peptide 2 Variants, Analogs, and Derivatives

Methods for Making Glucagon Like Peptide 2 Variants, Analogs, and Derivatives

Methods for peptides and proteins are well known in the art. GLP-2 may be prepared by a variety of techniques well known for generating peptides. GLP-2 which occurs naturally may be obtained by extraction from a natural source using an appropriate combination of protein isolation techniques. GLP-2 isolation and purification may, for example, be achieved by generating acid-ethanol extracts of ileal mucosa by a combination of size selection and HPLC-based fractionation. Alternatively, GLP-2 forms that incorporate only L-amino acids can be produced reproducibly and in commercial quantities using recombinant DNA technology. For this purpose, DNA coding for the desired form of GLP-2 is expressed in a microbial (e.g. yeast) or other cellular host, which is then cultured under conditions appropriate for GLP-2 expression. A variety of gene expression systems have been developed for this purpose and may drive expression of a desired gene using expression controls normally used by the chosen host. Since GLP-2 does not require post translational glycosylation for its activity, bacterial hosts such as E. coli may be used for its production. In such an embodiment, DNA coding for the selected GLP-2 is positioned such that it is operably linked to the lac, trp or PL genes of E. coli. GLP-2 may also be generated as a fusion protein in which the GLP-2 is linked releasably to a carrier protein that facilitates isolation and stability of the expression product.

In an approach universally applicable to the production of a selected GLP-2, and one used necessarily to produce GLP-2 forms that incorporate non-genetically encoded amino acids and N- and C-terminally derivatized forms, well established techniques of automated peptide synthesis are employed. See, for example, in J. M. Stewart and J. D. Young, Solid Phase Peptide Synthesis, 2nd Edition, 1984, Pierce Chemical Company, Rockford, Ill.; and in M. Bodanszky and A. Bodanszky, The Practice of Peptide Synthesis, 1984, Springer-Verlag, New York; Applied Biosystems 430A Users Manual, 1987, ABI Inc., Foster City, Calif. In these techniques, the GLP-2 is grown from its C-terminal, resin-conjugated residue by the sequential addition of appropriately protected amino acids, using either the Fmoc or tBoc protocols, as described for instance by Orskov et al. (1989, FEBS Letters 247:193).

Incorporation of N- and/or C-protecting group protocols, which is standard practice in solid phase peptide synthesis methods, may also be applied. For incorporation of C-terminal protecting groups, for example, synthesis of the desired peptide is typically performed using a supporting resin that has been chemically modified so that cleavage from the resin results in a peptide having the desired C-terminal protecting group. To provide peptides in which the C-terminus bears a primary amino protecting group, for instance, synthesis is performed using a p-methylbenzhydrylamine, (MBHA) resin so that, when peptide synthesis is completed, treatment with hydrofluoric acid releases the desired C-terminally amidated peptide. Similarly, incorporation of an N-methylamine protecting group at the C-terminus is achieved using N methylaminoethyl-derivatized DVB resin, which upon HF treatment releases peptides having an N-methylamidated C-terminus. Protection of the C-terminus by esterification can also be achieved using conventional procedures, involving use of a resin/blocking group combination that permits release of side-chain protected peptides from the resin, thereby allowing for subsequent reaction with the desired alcohol, to form the ester function. FMOC protecting groups, in combination with DVB resin derivatized with methoxyalkoxybenzyl alcohol or an equivalent linker can be used for this purpose, with cleavage from the support facilitated by TFA in dichloromethane. Esterification of the suitably activated carboxyl function e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once a desired peptide sequence has been synthesized, cleaved from the resin, and fully deprotected, the peptide is purified to ensure the recovery of a single oligopeptide having the selected amino acid sequence. Purification may be achieved using any of the standard approaches, which include reversed-phase high-pressure liquid chromatography (RP-HPLC) on alkylated silica columns. Such column fractionation is generally accomplished by running linear gradients, e.g. 10-90%, of increasing % organic solvent, e.g. acetonitrile, in aqueous buffer, usually containing a small amount (e.g. 0.1%) of pairing agent such as TFA or TEA. Alternatively, ion-exchange HPLC may be employed to separate peptide species on the basis of charge. Column fractions are collected and those containing peptide of the desired/required purity may be pooled. In one embodiment of the invention, the peptide is then treated in the established manner to exchange the cleavage acid (e.g. TFA) with a pharmaceutically acceptable acid, such as acetic, hydrochloric, phosphoric, maleic, tartaric, succinic and the like to provide a water soluble salt of the peptide.

For therapeutic use, the chosen GLP-2 or a pharmaceutically acceptable sale thereof is formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. See, for example, "Remington s Pharmaceutical Sciences", 17th Ed., Mack Publishing Company, Easton, Pa., 1995, for guidance on drug formulations. In one embodiment, the compounds are formulated for administration by infusion or by injection, either sub-cutaneously or intravenously, and are accordingly utilized as aqueous solutions in sterile and pyrogen-free form and optionally buffered to a slightly acidic or physiological pH. Thus, the compounds may be administered in distilled water, saline, buffered saline or 5% dextrose solution. Water solubility of compositions comprising GLP-2 may be enhanced by incorporating a solubility enhancer, such as acetic acid.

Sequences of Glucagon Like Peptide 2 Variants, Analogs, and Derivatives

GLP-2 suitable for inclusion in a formulation comprising GLP-2 according to some embodiments of the present invention may be any GLP-2 polypeptide or a pharmaceutically acceptable sale thereof. The GLP-2 polypeptide may be isolated from an animal source, or, alternatively, the GLP-2 may be recombinant. In some embodiments, the GLP-2 is human GLP-2. In some embodiments, the GLP-2 has the amino acid sequence set forth in SEQ ID NO. 1. In some embodiments, the GLP-2 is derivative of GLP-2. Such derivatives may exhibit improved properties such as, for example, increased stability. Such derivatives may by GLP-2 polypeptides having an altered amino acid sequence. Alternatively, such derivatives may be chemically altered. In some embodiments, such derivatives are disclosed in U.S. Pat. No. 5,789,379, the entire content of which is incorporated herein by reference.

A GLP-2 suitable for inclusion in a formulation comprising GLP-2 according to some embodiments of the present invention is disclosed in U.S. Pat. No. 5,990,077, the entire content of which is incorporated herein by reference. U.S. Pat. No. 5,990,077 discloses, for example, N-terminal and C-terminal blocking groups that may be incorporated into GLP-2 and derivatives thereof. U.S. Pat. No. 5,990,077 also discloses amino acid positions in GLP-2 wherein conservative amino acid changes can be made in the context of human and non-human GLP-2 sequences that do not adversely alter GLP-2 activity.

A GLP-2 suitable for inclusion in a formulation comprising GLP-2 according to some embodiments of the present invention is disclosed in U.S. Pat. No. 7,049,284, the entire content of which is incorporated herein by reference. U.S. Pat. No. 7,049,284 discloses, for example, a variety of GLP-2 variants having functional activity.

A GLP-2 suitable for inclusion in a formulation comprising GLP-2 according to some embodiments of the present invention is disclosed in U.S. Pat. No. 7,563,770, the entire content of which is incorporated herein by reference. U.S. Pat. No. 7,563,770 discloses, for example, optimized analogs of GLP-2 that are more stable due to resistance to dipeptidyl peptidase IV (DPP-IV) cleavage and exhibit enhanced activation of intestinotropic GLP-2 receptor binding.

A GLP-2 suitable for inclusion in a formulation comprising GLP-2 according to some embodiments of the present invention is disclosed in U.S. Patent Application Publication No. 2014/0377290, the entire content of which is incorporated herein by reference. U.S. 2014/0377290 discloses, for example, a GLP-2 conjugate that comprises GLP-2 and an immunoglobulin fragment crystalizable (Fc) domain, wherein the conjugate exhibits increased circulating half-life relative to GLP-2 due to reduced sensitivity to DPP-IV cleavage.

A GLP-2 suitable for inclusion in a formulation comprising GLP-2 according to some embodiments of the present invention is disclosed in International Patent Application Publication No. WO 2001049314 A2, the entire content of which is incorporated herein by reference.

A GLP-2 suitable for inclusion in a formulation comprising GLP-2 according to some embodiments of the present invention is disclosed in International Patent Application Publication No. WO 2002066511 A2, the entire content of which is incorporated herein by reference.

A GLP-2 suitable for inclusion in a formulation comprising GLP-2 according to some embodiments of the present invention is disclosed in U.S. Pat. No. 5,789,379.

GLP-2 and GLP-2 variants, derivatives, and analogs envisioned in accordance with the compositions and methods described herein comprise or consist of any one of or at least one of SEQ ID NOs: 1-3 and 6-62. In a particular embodiment, the GLP-2 is a peptide comprising or consisting of SEQ ID NO: 1, SEQ ID NO: 2, SEQ ID NO: 8, SEQ ID NOs: 11-59, or SEQ ID NO: 63. In another particular embodiment, the GLP-2 is a peptide comprising or consisting of SEQ ID NO: 2 or SEQ ID NO: 2.

GLP-2 and GLP-2 variants, derivatives, and analogs and compositions comprising GLP-2 or a GLP-2 variant, derivative, or analog may be administered via a variety of methods. Such methods include, without limitation, intravesicular, intralesional (in and around a lesion as described herein), oral, intravenous (iv), subcutaneous (sc or sq), intraperitoneal, intramuscular intradermal, rectal, nasal, or topical administration, or inhalation via nebulizer or inhaler, to the mammal in need thereof Therapeutic Dosing and Regimen The therapeutic dosing and regimen best suited for treatment of a subject (e.g., a human patient) vary with the disorder or condition to be treated, and according to the patient's weight and other parameters. A dose of GLP-2 or GLP-2 analog or GLP-2 derivative may be, for example, be administered at about 2.5 mg/kg, administered twice daily over 10 days. Smaller doses, e.g., in the µg/kg range, and shorter or longer duration or frequency of treatment, are also envisioned to produce therapeutically useful results, i.e., a statistically significant increase in epithelial cell proliferation in, e.g., the lower urinary tract or bladder. The dosage sizes and dosing regimen most appropriate for human use are based on, for example, U.S. Pat. No. 7,049,284, which is incorporated herein in its entirety by reference. It is, moreover, envisioned that localized administration to, e.g., the bladder, may be optimized based on the response of epithelial cells therein.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of GLP-2 normally circulating in the plasma, which typically varies from approximately 151 pmol/mL in the resting state to 225 pmol/mL after food intake for healthy adult humans. See, e.g., Orskow, C. and Helst, J. J., 1987, Scand. J. Clin. Lay. Invest. 47:165. Additional factors include the size, age, and general condition of the patient, the particular disorder being treated, the severity of the disorder, the presence of other drugs in the patient, the in vivo activity of the GLP-2 peptide. Trial dosages may be chosen after consideration of the results of animal studies and the clinical literature. It will be appreciated by a person of ordinary skill in the art that information such as binding constants and Ki derived from in vitro GLP-2 binding competition assays may also be used in calculating dosages.

A typical human dose of a GLP-2 peptide may be from about 10 µg/kg body weight/day to about 10 mg/kg/day, more particularly from about 50 µg/kg/day to about 5 mg/kg/day, and even more particularly about 100 µg/kg/day to 1 mg/kg/day.

As used herein, the term "intravesical administration" refers to the instillation or administration of an active ingredient (AI) or an active pharmaceutical ingredient (API) or a composition thereof into the bladder through a urethral catheter. Intravesical administration benefits from the ability to deliver a localized and precise dose of GLP-2 directly to the damaged bladder epithelial cells and tissue comprising same in need of GLP-2-mediated regenerative activity. Accordingly, in one embodiment, GLP-2 and GLP-2 variants, derivatives, and analogs and/or compositions comprising same are administered directly to the bladder via intravesicular adminstration. Direct administration to the bladder also reduces the potential for systemic side effects due to GLP-2 activity and also facilitates administration of minimal therapeutically effective doses of GLP-2 by virtue of assured delivery of the GLP-2 bolus to its intended target.

In a particular embodiment, GLP-2 and GLP-2 variants, derivatives, or analogs and/or compositions thereof are administered intravesicularly in a concentration range of 0.005 µM-10 µM; 0.0 µM-10 µM; 0.1 µM-10 µM; 0.2 µM-10 µM; 0.3 µM-10 µM; 0.4 µM-10 µM; 0.5 µM-10 µM; 0.6 µM-10 µM; 0.7 µM-10 µM; 0.8 µM-10 µM; 0.9 µM-10 µM; 1.0 µM-10 µM; 2.0 µM-10 µM; 3.0 µM-10 µM; 4.0 µM-10 µM; 5.0 µM-10 µM; 6.0 µM-10 µM; 7.0 µM-10 µM; 8.0 µM-10 µM; or 9.0 µM-10 µM. In a particular embodiment, GLP-2 and GLP-2 variants, derivatives, or analogs and/or compositions are administered intravesicularly in a concentration range of 0.01 µM-2 µM. In a still more particular embodiment, GLP-2 and GLP-2 variants, derivatives, or analogs and/or compositions are administered intravesicularly in a concentration range of 0.01 µM-1 µM. In another particular embodiment, GLP-2 and GLP-2 variants, derivatives, or analogs and/or compositions are administered intravesicularly in a concentration range of about 0.1 µM.

As described in connection with other therapeutic regimens, GLP-2 and GLP-2 variants, derivatives, or analogs and/or compositions thereof may be adminstered intravesicularly in a therapeutically effective amount at least once per day, twice per week, once per week, or on a monthly basis. For an intravesicular treatment regimen, a GLP-2 receptor agonist (e.g., GLP-2 or variant, derivative, or analog thereof) may be administered in a therapeutically effective amount at a higher dose relative to doses used for systemic administration and localized administration may be administered at a high frequency (e.g., once per day), at low frequency (e.g., once per week, once every two weeks, or once per month), or intermittently. In an embodiment wherein a GLP-2 receptor agonist is administered intermittently, it may be administered once per day for a week, which is followed by a period wherein the GLP-2 receptor agonist is not administered for some intervening time (rest period). Intervening time between treatment cycles may be optimized based on the disorder being treated and a medical practitioner's opinion.

In another embodiment, GLP-2 and/or GLP-2 variants, derivatives, and analogs and/or compositions comprising same are administered directly to the bladder via submucosal injection. As described in, for example, Cox et al. (2009, The Canadian J Urology 16; ISSN: 1195-9479; 204; which is incorporated herein by reference in its entirety), a therapeutic agent or composition thereof may be injected into the submucosal space of Hunner's ulcers using an endoscopic needle. As is understood in the art, Hunner's ulcer subtype interstitial cystitis/bladder pain syndrome is diagnosed by cystoscopic examination that reveals denuded epithelium, ulceration, and submucosal inflammation.

In another embodiment, GLP-2 and/or GLP-2 variants, derivatives, and analogs and/or compositions comprising same are administered using a kidney-targeted drug delivery system such as those described in Zhou et al. (2013, Acta Pharmaceutica Sinica B 4:37-42; the entire content of which is incorporated herein by reference) and Sarko and Georges (2016, J Anal Pharm Res 2:00033; the entire content of which is incorporated herein by reference).

Therapeutic efficacy of GLP-2 and GLP-2 variants, derivatives, and analogs and/or compositions comprising same may be determined by evaluating and comparing patient symptoms and quality of life pre- and post-administration. Such methods apply irrespective of the mode of administration. In a particular embodiment, pre-administration refers to evaluating patient symptoms and quality of life prior to onset of therapy and post-administration refers to evaluating patient symptoms and quality of life at least 2-8 weeks after onset of therapy. In a particular embodiment, the post-administration evaluating is performed about 2-8, 2-6, 4-6, or 4 weeks after onset of therapy. In a particular embodiment, patient symptoms and quality of life pre- and post-administration are evaluated via questionnaire assessment. Such questionnaires are known in the art and include, without limitation, the International Prostate Symptom Score (IPSS), the Pelvic Pain and Urgency/Frequency (PUF) symptom scale, and the Patient Global Impression of Change (PGIC). Clinical symptoms assessed in the IPSS questionnaire include: incomplete emptying, frequency, intermittence, urgency, weak stream, nocturia, and quality of life (QOL). Clinical symptoms assessed in the PUF questionnaire include: daytime voids, nighttime voids, bothersome nighttime voids, symptoms during sex, avoidance of sex, pain in the bladder and/or pelvis, pain scale, bother scale, urgency after voiding, urgency scale, bother scale, total pain scale, total bother scale. The above questionnaires are known in the art and described in Cox et al. (2009, supra; which is incorporated herein by reference).

Additional evaluations of therapeutic efficacy may be based on analyses of fresh catheterized urine samples taken from patients pre- and post-therapeutic intervention. Urine samples may be processed to generate urine sediment, which can be analyzed via, for example, use of microarrays to evaluate gene expression levels for the presence of or upregulation of indicators of inflammation. Such assays are described in, for example, Blalock et al. (2012, J Urology 187:725-732; the entire content of which is incorporated herein by reference).

In some embodiments, the formulation comprising GLP-2 comprises one or more additional components, wherein the additional component is at least one of an osmolar component that provides an isotonic, or near isotonic solution compatible with human cells or blood, a compound that adheres the formulation comprising GLP-2 to the surface of the bladder epithelium, an antibacterial agent, an antifungal agent, a vasoconstrictor; an anti-inflammatory agent; and a preservative.

In some embodiments, the formulation comprising GLP-2 is in the form of a sustained release formulation and further comprises one or more additional components, wherein the additional component is at least one of an antibacterial agent, an antifungal agent, a vasoconstrictor; an anti-inflammatory agent; and a preservative.

In some embodiments, the sustained release formulation is administered as a suppository. An exemplary suppository formulation is disclosed in U.S. Pat. No. 8,741,330, the entire content of which is incorporated herein by reference.

In some embodiments, the sustained release formulation is administered in an implant designed for subcutaneous (sc or sq) implantation. Exemplary sc implants are known to those of skill in the art and may involve a port or catheter or the like.

In some embodiments, the sustained release formulation is administered via continuous local therapy such as that achieved by the TARTS® system. The TARIS® system is a controlled release dosage form designed for delivery of an API to the bladder. In one embodiment, it is a dual-lumen silicone tube, which contains a solid drug core in one lumen and a superelastic wireform in the other to impart shape. An API encompassed therein is delivered passively from the system, thereby achieving continuous release of the API in the bladder over a period of weeks to months. API release can be tailored to match the needs of a specific treatment regimen in accordance with a medical practitioner's recommendations.

In some embodiments, the formulation comprising GLP-2 is buffered to neutralize the acidic urine. Examples of buffers are disclosed in U.S. Pat. No. 5,612,313. In some embodiments, the pH of the formulation comprising GLP-2 is in the range of 6.8 to 8.3. In some embodiments, the pH of the formulation comprising GLP-2 is from 7.2 to 7.6. In some embodiments, the pH of the formulation comprising GLP-2 is from 7.3 to 7.5.

Examples of buffering compounds suitable for inclusion in a formulation comprising GLP-2 according to some embodiments of the present invention are disclosed in U.S. Pat. No. 7,414,039, the entire content of which is incorporated herein by reference.

In some embodiments, the osmolar component is a salt, such as sodium chloride, or a sugar or a combination of two or more of these components. In some embodiments, the sugar may be a monosaccharide such as dextrose, a disaccharide such as sucrose or lactose, a polysaccharide such as dextran 40, dextran 60, or starch, or a sugar alcohol such as mannitol. The osmolar component is readily selected by those skilled in the art. Examples of osmolar components suitable for inclusion in a formulation comprising GLP-2 according to some embodiments of the present invention are disclosed in International Patent Application Publucation No. WO 2014/171986, the entire content of which is incorporated herein by reference.

In some embodiments, the antibacterial agent is at least one of a sulfonamide, penicillin, a combination of trimethoprim plus sulfamethoxazole, a quinolone, methenamine, nitrofurantoin, a cephalosporin, a carbapenem, an aminoglycoside, a tetracycline, and a macrolide. Examples of antibacterial agents suitable for inclusion in a formulation comprising GLP-2 according to some embodiments of the present invention are disclosed in International Patent Application Publucation No. WO 2014/171986, the entire content of which is incorporated herein by reference.

In some embodiments, the antifungal agent is at least one of amphotericin B, itraconazole, ketoconazole, fluconazole, miconazole, and flucytosine.

In some embodiments, the compound that adheres the formulation comprising GLP-2 to the surface of the bladder epithelium is an activatable gelling agent. In some embodiments, the activatable gelling agent is a thermoreversible gelling agent. In some embodiments, the thermoreversible gelling agent is at least one of Pluronics F127 gel, Lutrol gel, N-isopropylacrylamide, ethylmethacrylate, N-acryloxysuccinimide, xyloglucan sols of 1-2%, graft copolymers of pluronic and poly(acrylic acid), pluronicchitosan hydrogels, and a poly(ethylene glycol)-poly[lactic acid-co-glycolic acid]poly(ethylene glycol) (PEG-PLGA-PEG) copolymer. Examples of thermoreversible gelling agents suitable for inclusion in a formulation comprising GLP-2 according to some embodiments of the present invention are disclosed in International Patent Application Publication No. WO 2014/171986, the entire content of which is incorporated herein by reference.

In some embodiments, the anti-inflammatory agent is at least one of hydrocortisone, cortisone, beclomethasone dipropionate, betamethasone, dexamethasone, prednisone, methylprednisolone, triamcinolone, fluocinolone acetonide, fludrocortisone, aspirin, sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac. Examples of anti-inflammatory agents suitable for inclusion in a formulation comprising GLP-2 according to some embodiments of the present invention are disclosed in International Patent Application Publucation No. WO 2014/171986, the entire content of which is incorporated herein by reference.

In some embodiments, the preservative is at least one of parabens, chlorobutanol, phenol, sorbic acid, and thimerosal.

In some embodiments, a formulation comprising GLP-2 further comprises a heparinoid. Hepariniods suitable for inclusion into a formulation comprising GLP-2 according to some embodiments of the present invention are disclosed in U.S. Pat. No. 7,414,039, the entire content of which is incorporated herein by reference.

In some embodiments, a formulation comprising GLP-2 further comprises a topical anaesthetic. Topical anaesthetics suitable for inclusion in a formulation comprising GLP-2 according to some embodiments of the present invention are disclosed in U.S. Pat. No. 7,414,039, the entire content of which is incorporated herein by reference.

Treatment:

In certain embodiments, a method is provided for treating and/or ameliorating a disorder of the lower urinary tract, comprising administering a composition comprising GLP-2 described herein to a patient in need thereof in an amount sufficient to treat and/or ameliorate lower urinary tract disorder.

In some embodiments, the disorder of the lower urinary tract comprises at least one of inflammation of the bladder wall, bacterial cystitis, fungal cystitis, urethral syndrome, chronic pelvic pain syndrome, hemorrhagic cystitis, radiation-induced cystitis, chemotherapy-induced cystitis, interstitial cystitis/bladder pain syndrome, overactive bladder, and Hunner's lesions.

In some embodiments, the amount sufficient to treat and/or ameliorate the lower urinary tract disorder is from $1 \times 10^{-11}$ mol/l to $1 \times 10^{-5}$ mol/l GLP-2 receptor agonist (e.g., but not limited to, SEQ ID NO: 1, SEQ ID NO: 2, an amino terminal acetylated, carboxy terminal amidated, pegylated, or glycolsylated SEQ ID NO: 1 or SEQ ID NO: 2, or any combination thereof) per dose. In some embodiments, the amount sufficient to treat and/or ameliorate the lower urinary tract disorder is from $1\times10^{-10}$ mol/l to $1\times10^{-5}$ mol/l GLP-2 receptor agonist per dose. In some embodiments, the amount sufficient to treat and/or ameliorate the lower urinary tract disorder is from $1\times10^{-9}$ mol/l to $1\times10^{-5}$ mol/l GLP-2 receptor agonist per dose. In some embodiments, the amount sufficient to treat and/or ameliorate the lower urinary tract disorder is from $1\times10^{-8}$ mol/l to $1\times10^{-5}$ mol/l GLP-2 receptor agonist per dose. In some embodiments, the amount sufficient to treat and/or ameliorate the lower urinary tract disorder is from $1\times10^{-7}$ mol/l to $1\times10^{-5}$ mol/l GLP-2 receptor agonist per dose. In some embodiments, the amount sufficient to treat and/or ameliorate the lower urinary tract disorder is from $1\times10^{-6}$ mol/l to $1\times10^{-5}$ mol/l GLP-2 receptor agonist per dose.

In some embodiments, the amount sufficient to treat and/or ameliorate the lower urinary tract disorder is from $1\times10^{-11}$ mol/l to $1\times10^{-6}$ mol/l GLP-2 receptor agonist per dose. In some embodiments, the amount sufficient to treat and/or ameliorate the lower urinary tract disorder is from $1\times10^{-11}$ mol/l to $1\times10^{-7}$ mol/l GLP-2 receptor agonist per dose. In some embodiments, the amount sufficient to treat and/or ameliorate the lower urinary tract disorder is from $1\times10^{-11}$ mol/l to $1\times10^{-8}$ mol/l GLP-2 receptor agonist per dose. In some embodiments, the amount sufficient treat and/or ameliorate the lower urinary tract disorder is from $1\times10^{-11}$ mol/l to $1\times10^{-9}$ mol/l GLP-2 receptor agonist per dose. In some embodiments, the amount sufficient to treat and/or ameliorate the lower urinary tract disorder is from $1\times10^{-11}$ mol/l to $1\times10^{-10}$ mol/l GLP-2 receptor agonist per dose.

In some embodiments, the amount sufficient to treat and/or ameliorate the lower urinary tract disorder is from $1\times10^{-10}$ mol/l to $1\times10^{-6}$ mol/l GLP-2 receptor agonist per dose. In some embodiments, the amount sufficient treat and/or ameliorate the lower urinary tract disorder is from $1\times10^{-9}$ mol/l to $1\times10^{-7}$ mol/l GLP-2 receptor agonist per dose. In some embodiments, the amount sufficient treat and/or ameliorate the lower urinary tract disorder is from $1\times10^{-7}$ mol/l to $1\times10^{-8}$ mol/l GLP-2 receptor agonist per dose. In some embodiments, the patient receives a single dose of GLP-2 receptor agonist per day. In some embodiments, patient receives more than one dose of GLP-2 receptor agonist per day. In other embodiments, a GLP-2 receptor agonist is administered in a therapeutically effective amount twice per week, once per week, or on a monthly basis. For a localized treatment regimen, a GLP-2 receptor agonist may be administered in a therapeutically effective amount at a higher dose relative to doses used for systemic administration and localized administration may be administered at a high frequency (e.g., once per day), at low frequency (e.g., once per week, once every two weeks, or once per month), or intermittently. In an embodiment wherein a GLP-2 receptor agonist is administered intermittently, it may be administered once per day for a week, which is followed by a period wherein the GLP-2 receptor agonist is not administered for some intervening time (rest period). Intervening time between treatment cycles may be optimized based on the disorder being treated and a medical practitioner's opinion.

In some embodiments, the amount sufficient to treat and/or ameliorate the lower urinary tract disorder is from $1\times10^{-11}$ mol/l to $1\times10^{-5}$ mol/l GLP-2 (e.g., SEQ ID NO: 2) per dose. In some embodiments, the amount sufficient to treat and/or ameliorate the lower urinary tract disorder is from $1\times10^{-10}$ mol/l to $1\times10^{-5}$ mol/l GLP-2 per dose. In some embodiments, the amount sufficient to treat and/or ameliorate the lower urinary tract disorder is from $1\times10^{-9}$ mol/l to $1\times10^{-5}$ mol/l GLP-2 per dose. In some embodiments, the amount sufficient to treat and/or ameliorate the lower urinary tract disorder is from $1\times10^{-8}$ mol/l to $1\times10^{-5}$ mol/l GLP-2 per dose. In some embodiments, the amount sufficient to treat and/or ameliorate the lower urinary tract disorder is from $1\times10^{-7}$ mol/l to $1\times10^{-5}$ mol/l GLP-2 per dose. In some embodiments, the amount sufficient to treat and/or ameliorate the lower urinary tract disorder is from $1\times10^{-6}$ mol/l to $1\times10^{-5}$ mol/l GLP-2 per dose. In some embodiments, the patient receives a single dose of GLP-2 receptor agonist per day. In some embodiments, patient receives more than one dose of GLP-2 receptor agonist per day. In other embodiments, a GLP-2 receptor agonist is administered in a therapeutically effective amount twice per week, once per week, or on a monthly basis. For a localized treatment regimen, a GLP-2 receptor agonist may be administered in a therapeutically effective amount at a higher dose relative to doses used for systemic administration and localized administration may be administered at a high frequency (e.g., once per day), at low frequency (e.g., once per week, once every two weeks, or once per month), or intermittently. In an embodiment wherein a GLP-2 receptor agonist is administered intermittently, it may be administered once per day for a week, which is followed by a period wherein the GLP-2 receptor agonist is not administered for some intervening time (rest period). Intervening time between treatment cycles may be optimized based on the disorder being treated and a medical practitioner's opinion.

In some embodiments, the amount sufficient to treat and/or ameliorate the lower urinary tract disorder is from $1\times10^{-11}$ mol/l to $1\times10^{-6}$ mol/l GLP-2 per dose. In some embodiments, the amount sufficient to treat and/or ameliorate the lower urinary tract disorder is from $1\times10^{-11}$ mol/l to $1\times10^{-7}$ mol/l GLP-2 per dose. In some embodiments, the amount sufficient to treat and/or ameliorate the lower urinary tract disorder is from $1\times10^{-11}$ mol/l to $1\times10^{-8}$ mol/l GLP-2 per dose. In some embodiments, the amount sufficient to treat and/or ameliorate the lower urinary tract disorder is from $1\times10^{-11}$ mol/l to $1\times10^{-9}$ mol/l GLP-2 per dose. In some embodiments, the amount sufficient to treat and/or ameliorate the lower urinary tract disorder is from $1\times10^{-11}$ mol/l to $1\times10^{-10}$ mol/l GLP-2 per dose. In some embodiments, the patient receives a single dose of GLP-2 receptor agonist per day. In some embodiments, patient receives more than one dose of GLP-2 receptor agonist per day. In other embodiments, a GLP-2 receptor agonist is administered in a therapeutically effective amount twice per week, once per week, or on a monthly basis. For a localized treatment regimen, a GLP-2 receptor agonist may be administered in a therapeutically effective amount at a higher dose relative to doses used for systemic administration and localized administration may be administered at a high frequency (e.g., once per day), at low frequency (e.g., once per week, once every two weeks, or once per month), or intermittently. In an embodiment wherein a GLP-2 receptor agonist is administered intermittently, it may be administered once per day for a week, which is followed by a period wherein the GLP-2 receptor agonist is not administered for some intervening time (rest period). Intervening time between treatment cycles may be optimized based on the disorder being treated and a medical practitioner's opinion.

In some embodiments, the amount sufficient to treat and/or ameliorate the lower urinary tract disorder is from $1\times10^{-10}$ mol/l to $1\times10^{-6}$ mol/l GLP-2 per dose. In some embodiments, the amount sufficient to treat and/or ameliorate the lower urinary tract disorder is from $1\times10^{-9}$ mol/l to $1 \times 10^{-7}$ mol/l GLP-2 per dose. In some embodiments, the amount sufficient to treat and/or ameliorate the lower urinary tract disorder is from $1 \times 10^{-7}$ mol/l to $1 \times 10^{-8}$ mol/l GLP-2 per dose. In some embodiments, the amount sufficient to treat and/or ameliorate the lower urinary tract disorder is from $1 \times 10^{-10}$ mol/l to $1 \times 10^{-8}$ mol/l GLP-2 per dose. In some embodiments, the dose is divided and administered more than one time per day to result in an administration of $1 \times 10^{-11}$ mol/l to $1 \times 10^{-7}$ mol/l GLP-2 receptor agonist in a single day. In some embodiments, the patient receives a single dose of GLP-2 receptor agonist per day. In some embodiments, patient receives more than one dose of GLP-2 receptor agonist per day. In other embodiments, a GLP-2 receptor agonist is administered in a therapeutically effective amount twice per week, once per week, or on a monthly basis. For a localized treatment regimen, a GLP-2 receptor agonist may be administered in a therapeutically effective amount at a higher dose relative to doses used for systemic administration and localized administration may be administered at a high frequency (e.g., once per day), at low frequency (e.g., once per week, once every two weeks, or once per month), or intermittently. In an embodiment wherein a GLP-2 receptor agonist is administered intermittently, it may be administered once per day for a week, which is followed by a period wherein the GLP-2 receptor agonist is not administered for some intervening time (rest period). Intervening time between treatment cycles may be optimized based on the disorder being treated and a medical practitioner's opinion.

In some embodiments, the patient receives an effective amount of GLP-2 receptor agonist per day for more than one day. In some embodiments, the patient receives an effective amount of GLP-2 receptor agonist per day until the symptoms of the lower urinary tract disorder improve.

Animal Models

Various animal models for urinary bladder disorders, conditions, and diseases have been described, including: a nonhuman primate model of urinary bladder regeneration (Sharma et al. 2011, Stem Cells 29:241-250; the entire content of which is incorporated herein by reference); animal models of overactive bladder research (Parsons and Drake. 2011, Handbookd of Exp Pharmacol 202:15-43; the entire content of which is incorporated herein by reference); and experimental animal models of neurogenic bladder dysfunction (Yoo and Lee. 2010, Intern. Neurourology J 4:1-6; the entire content of which is incorporated herein by reference). GLP-2 and variants, derivatives, and analogs thereof may be tested in known animal models and evaluated therein for efficacy and optimization thereof by adjusting the dose of GLP-2 (or a variant, derivative, or analog thereof), mode of administration, therapeutic regimen (e.g., timing and periodicity of administration), and potential for combination with other therapeutic agents.

The present invention is further illustrated, but not limited by, the following examples.

EXAMPLES

Therapeutically effective ranges of GLP-2 can be determined for various target tissue/cells. As indicated hereinabove, cellular response to GLP-2 depends on the presence of GLP-2 receptors on the cell surface in sufficient numbers to trigger intracellular signaling pathways downstream of the GLP-2 receptors. Target tissue/cellular responses to GLP-2 may, for example, be measured by evaluating markers of cellular proliferation and growth. Various markers of cell proliferation and growth are known in the art and comprise, for example, an increase in cell number, [3H]-thymidine incorporation into cellular DNA, and total protein content. [3H]-thymidine incorporation into cellular DNA has, for example, been used as a marker for cell growth in transitional epithelium of the bladder. Gene expression studies have also been used to show arsenic mediated cell proliferation in cultured UROtsa, a SV40 immortalized human urothelium cell line.

In Vivo GLP-2 Treatment of Chemically Damaged Murine Bladder Epithelium

Several studies across different species have shown in vivo effects of GLP-2 on intestinal epithelial growth. Much of this work has been conducted in murine and rat models looking at total intestinal weight, mucosal thickness, villus growth, total DNA, reduced inflammation and the presence of microscopic lesions in normal and treated rat inflammatory bowel disease models and ischemic reperfusion injured mice. In all cases treatment with GLP-2 enhanced intestinal/mucosal mass and attenuated damage in the intestinal disease models examined.

In vivo studies on bladder epithelial cell regeneration, although not numerous, have been described and offer animal model systems in which to examine the effects of various agents for their potential as therapeutic agents for promoting regeneration of epithelial cells in the bladder. Mysorekar et al. (2002, J Biol Chem 277:7412-7419; the entire content of which is incorporated herein by reference) investigated molecular mechanisms of bladder epithelium renewal following infection by Uropathogenic *Escherichia coli*. Using DNA microarray analysis, Mysorekar et al. found that several molecular regulators involved in the reconstitution of the urothelium were up regulated in response to damage. In another study, Lavelle et al. (2001, Urology 57:113; the entire content of which is incorporated herein by reference) describe the development and use of a model wherein IC is induced by protamine sulfate in small animals. Protamine sulfate treatment results in temporary disruption of the bladder epithelium. Normal bladder function/structure returns within 5 days of treatment. Each of the above models is envisioned as a suitable test assay in which to assess GLP-2-induced bladder epithelial cell proliferation/regeneration in vivo.

In Vitro Study Testing Cell Proliferation

URG-801/GLP-2 mediated cell proliferation was detected by assaying BrdU incorporation into DNA using non-tumorigenic primary human bladder epithelial cells. An exemplary non-tumorigenic primary human bladder epithelial cell line is ATCC-PCS-420-010, which may be purchased from the American Type Culture Collection (ATCC) repository. Briefly, ATCC-PCS-420-010 cells were starved for 48 hours in low nutrient (0.5%) medium and then GLP-2 was added to the culture medium at the indicated concentrations and the cells were cultured for an additional 24 hours in the presence of GLP-2. As indicated in the timeline presented in FIG. 1, bromodeoxyuridine (BrdU) was added concurrently with the GLP-2. As shown in FIG. 1, GLP-2 induced a dose dependent increase in DNA synthesis as measured by BrdU incorporation.

Figure 2:
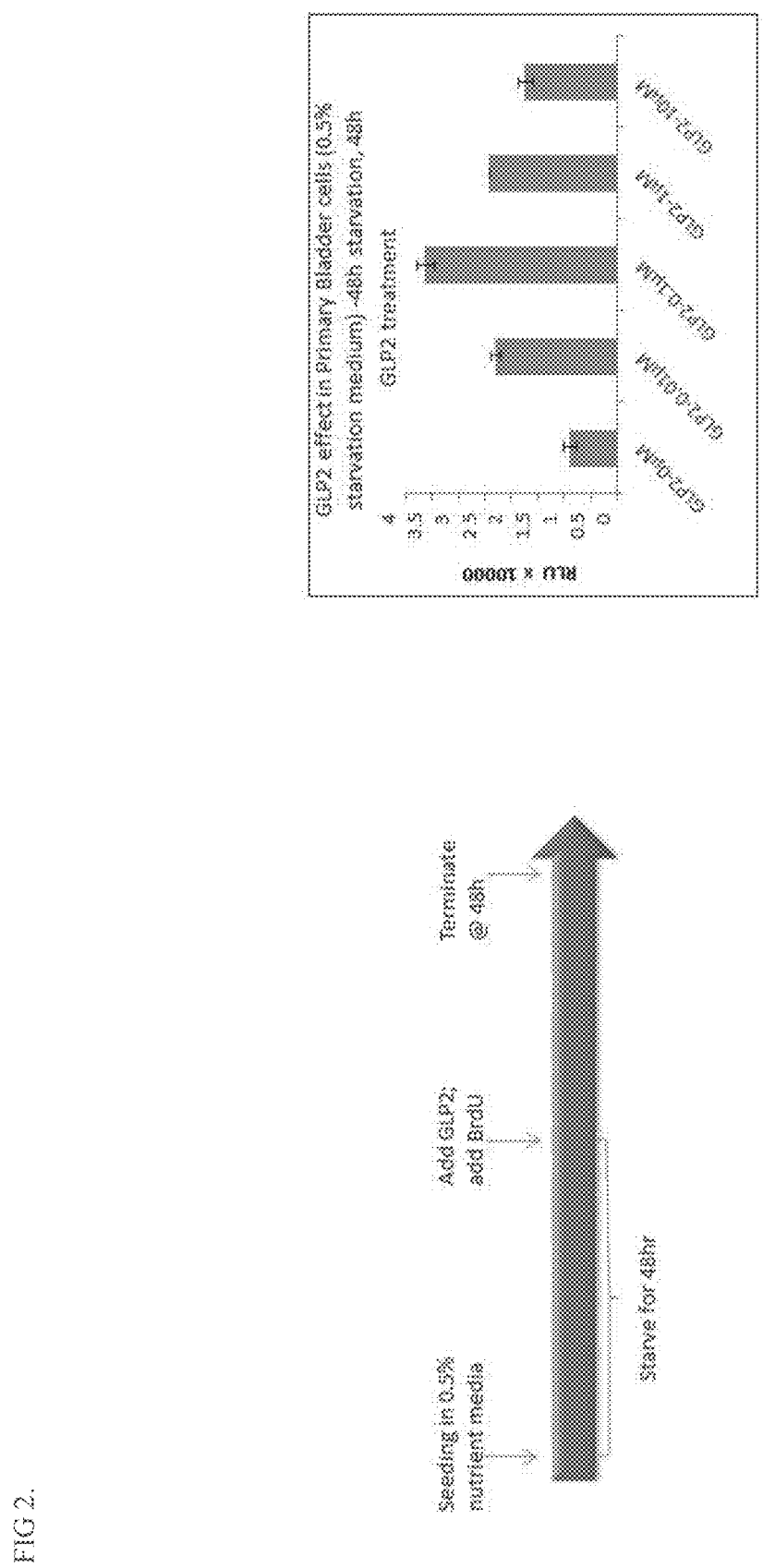
FIG. 2 presents a histogram plot depicting results from a BrdU cell proliferation assay. Primary human bladder epithelial cells were nutrient starved as indicated and treated with GLP-2 for 48 hours at the indicated concentrations.

To investigate further parameters affecting GLP-2 induced bladder epithelial cell proliferation, the duration of culturing in the presence of GLP-2 was extended. In this experimental protocol, ATCC-PCS-420-010 cells were starved for 48 hours in low nutrient (0.5%) medium and then GLP-2 was added to the culture medium at the indicated concentrations and the cells were cultured for ab additional 48 hours in the presence of GLP-2. As indicated in the timeline presented in FIG. 2, BrdU was added concurrently with the GLP-2. As shown in FIG. 2, GLP-2 induced a dose dependent increase in DNA synthesis as measured by BrdU incorporation that peaked at 0.1 µM GLP-2. The bell shaped curve of the relationship of BrdU incorporation and GLP-2 concentration suggests that concentrations of about 0.1 µM GLP-2 may be particularly effective when cells are incubated for prolonged periods of time under conditions of duress, such as nutrient depletion. These results may be predictive of in vivo responses of bladder epithelial cells.

Additional concentrations of GLP-2 may be evaluated, including GLP-2 concentrations ranging from $1\times10^{-11}$-$1\times10^{-7}$ mol/L (e.g., $1\times10^{-11}$, $1\times10^{-10}$, $1\times10^{-9}$, $1\times10^{-8}$ and $1\times10^{-7}$ mol/L), in the context of bladder epithelial cell proliferative responses. As per standard practice, cellular response would be compared to that observed with a vehicle control. ATCC-PCS-420-010 cells or additional exemplary bladder epithelial cell lines may be used in such experiments. Exemplary bladder epithelial cells also include freshly isolated bladder epithelial cells and particularly those that have been isolated from animal models of disorders/ conditions characterized by damage to bladder epithelial cells. See also Example 5. As indicated herein, bladder epithelial cells may be cultured under conditions of stress (e.g., nutrient depletion) for multiple time points, including 24 hours, 48 hours, and 72 hours. BrdU incorporation may be measured in GLP-2 treated cells and compared with that observed in vehicle control treated cells. In a particular embodiment, freshly isolated bladder epithelial cells isolated from animal models of disorders/conditions characterized by damage to bladder epithelial cells have experienced damage in vivo and are isolated and treated with GLP-2 alone or in combination with other therapeutic agents ex vivo.

Ex Vivo Study Testing Administration of GLP-2

Surface umbrella cells of rat bladders may be selectively damaged with protamine sulfate (PS) (10 mg/mL in phosphate buffered saline) administered intravesically for 15 minutes into anesthetized female rates according to the methods disclosed in Lavelle et al. (2001, supra). In one embodiment, GLP-2 is added 24 hours after PS treatment, when the bladder damage is maximal. The bladders of the female mice may be excised after 24 to 48 hours of GLP-2 treatment and analyzed. The test groups envisioned are as follows:

(1) 24 hours post-PS treatment: 4 groups from PS treated rats (3 GLP-2 concentrations and 1 vehicle control) and 1 group untreated control.

(2) 48 hours post-PS treatment: 4 groups from PS treated rats (3 GLP-2 concentrations and 1 vehicle control) and 1 group untreated control.

Bladder epithelial cells may be evaluated using a variety of methods indicated herein, including those relating to proliferative response (e.g., BrdU and [3H]-thymidine incorporation) and those directed to evaluating tissue regenerative capacity, tissue integrity, and/or expression of cellular proteins indicative of cell status/health (e.g., histological analysis, with and without staining for various cellular markers, including epithelial cell markers and western blot analysis).

Urothelial Cell Regeneration Studies

Culture conditions may be optimized for maintaining the primary normal urothelial cell line A/T/N and two transitional bladder cell lines 5637 and T24 (cell lines A/T/N, 5637, and T24 are available from the ATCC) to facilitate their use in studying urothelial cell regeneration. These three ATCC urothelial cell lines may, for example, be maintained in 2D culture and examined after treatment with GLP-2 for effects on cell proliferation, stemness, GLP-2 receptor (GLP-2R) upregulation, and regeneration in the presence or absence of urothelial insult (e.g., treatment with protamine sulfate) using molecular and imaging studies. In that the urothelium is an example of transitional epithelium that lines most of the urinary tract, including the bladder, the ureters, the renal pelvis, and parts of the urethra, GLP-2 is likely to have a similar proliferative effect on urothelial cells as observed with epithelial cell lines.

In another embodiment, patient-derived and urothelial cell-derived micro-tissues may be maintained as spheres or organoids to evaluate the growth promoting and regenerative effects of GLP-2 in 3D culture. The A/T/N, 5637, and T24 cell lines and de-identified patient-derived urothelial cells may be used for 3D organoid culture using known protocols that may be optimized for these cells/cell lines based standard techniques known in the art pertaining to 3D organoids and/or spheres. The effects of GLP-2 on organoid initiation and stem cell regenerative effects may be examined in such 3D cultures. Intracellular ATP, cell size, and protein content and staining may be used to characterize the presence, expression level, and activity of GLP-2R, and proliferation and bladder specific markers. These studies may be repeated in at least two additional patient derived samples.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method for treating a subject afflicted by a disorder of the lower urinary tract epithelium, wherein the disorder is characterized by damage to epithelial cells in the lower urinary tract epithelium of the subject, the method comprising administering to the subject a therapeutically effective amount of a GLP-2, a GLP-2 derivative, or a GLP-2 analog, wherein the GLP-2, the GLP-2 derivative, or the GLP-2 analog comprise SEQ ID NO: 1, SEQ ID NO: 2, an amino terminal acetylated, carboxy terminal amidated, pegylated, or glycosylated SEQ ID NO: 1 or an amino terminal acetylated, carboxy terminal amidated, pegylated, or glycosylated SEQ ID NO: 2, wherein the therapeutically effective amount of the GLP-2, a GLP-2 derivative, or a GLP-2 analog is sufficient to promote proliferation of the epithelial cells in the lower urinary tract epithelium of the subject, thereby treating the disorder of the lower urinary tract epithelium in the subject.

2. The method of claim 1, wherein the disorder of the lower urinary tract epithelium comprises at least one of hemorrhagic cystitis, or interstitial cystitis/bladder pain syndrome.

3. The method of claim 2, wherein the interstitial cystitis/bladder pain syndrome comprises Hunner's lesions.

4. A method for promoting regeneration of urothelium in a subject, wherein the urothelium is characterized by damage to epithelial cells in the uroepithelium, the method comprising administering to the subject a therapeutically effective amount of a GLP-2, a GLP-2 derivative, or a GLP-2 analog, wherein the GLP-2, the GLP-2 derivative, or the GLP-2 analog comprise SEQ ID NO: 1, SEQ ID NO: 2, an amino terminal acetylated, carboxy terminal amidated, pegylated, or glycosylated SEQ ID NO: 1 or an amino terminal acetylated, carboxy terminal amidated, pegylated, or glycosylated SEQ ID NO: 2, wherein the therapeutically effective amount of the GLP-2, a GLP1-2 derivative, or a GLP-2 analog is sufficient to promote proliferation of the epithelial cells in the uroepithelium of the subject, thereby promoting regeneration of urothelium in the subject.

5. The method of claim 4, wherein the damage to epithelial cells in the subject's uroepithelium is associated with at least one of hemorrhagic cystitis, interstitial cystitis/bladder pain syndrome, or overactive bladder.

6. The method of claim 5, wherein the interstitial cystitis/bladder pain syndrome comprises Hunner's lesions.

7. The method of claim 1, wherein the subject is a mammal.

8. The method of claim 1, wherein the subject is a human.

9. The method of claim 1, wherein the GLP-2, the GLP-2 derivative, or the GLP-2 analog is administered intravesicularly, intralesionally, orally, intravenously, intraperitoneally, intramuscularly, subcutaneously, intradermally, rectally, nasally, topically, or by inhalation via nebulizer or inhaler to the subject.

10. The method of claim 1, wherein the GLP-2, the GLP-2 derivative, or the GLP-2 analog is administered directly to the subject's lower urinary tract.

11. The method of claim 1, wherein the GLP-2, the GLP-2 derivative, or the GLP-2 analog is administered directly to the subject's bladder.

12. The method of claim 3, wherein the GLP-2, the GLP-2 derivative, or the GLP-2 analog is administered directly to the Hunner's lesions of the subject.

13. The method of claim 1, wherein the disorder of the subject's lower urinary tract epithelium is due to an injury comprising at least one of a chemical insult, mechanical insult, or disease.

14. The method of claim 13, wherein the disease is a urinary tract infection.

15. The method of claim 1, wherein the GLP-2, the GLP-2 derivative, or the GLP-2 analog is formulated with a gelling agent and is administered directly to the subject's bladder.

16. The method of claim 1, wherein the GLP-2, the GLP-2 derivative, or the GLP-2 analog is administered at a does in a range of 10 µg/kg body weight/day to about 10 mg/kg/day.

17. The method of claim 1, further comprising administering at least one additional therapeutic agent, wherein the at least one additional therapeutic agent comprises at least one of an anti-microbial agent, a heparanoid, a topical anesthetic, an anti-inflammatory agent, a systemic analgesic, or an inhibitor of neuropathic pain.

* * * * *